(12) United States Patent
Palmer

(10) Patent No.: US 11,160,639 B2
(45) Date of Patent: Nov. 2, 2021

(54) DENTAL ALIGNMENT SYSTEM AND METHOD FOR DENTAL IMPLANT PLACEMENT

(71) Applicant: Mark Elliot Palmer, Alpharetta, GA (US)

(72) Inventor: Mark Elliot Palmer, Alpharetta, GA (US)

( * ) Notice: Subject to any disclaimer, the term of this patent is extended or adjusted under 35 U.S.C. 154(b) by 344 days.

(21) Appl. No.: 15/913,425

(22) Filed: Mar. 6, 2018

(65) Prior Publication Data

US 2019/0223988 A1   Jul. 25, 2019

Related U.S. Application Data

(60) Provisional application No. 62/619,483, filed on Jan. 19, 2018, provisional application No. 62/629,427, filed on Feb. 12, 2018.

(51) Int. Cl.

| | |
|---|---|
| *A61C 1/08* | (2006.01) |
| *A61C 8/00* | (2006.01) |
| *A61C 13/34* | (2006.01) |
| *A61C 13/00* | (2006.01) |
| *A61B 6/14* | (2006.01) |
| *A61C 13/107* | (2006.01) |

(52) U.S. Cl.
CPC .............. *A61C 8/0089* (2013.01); *A61B 6/14* (2013.01); *A61C 1/084* (2013.01); *A61C 8/001* (2013.01); *A61C 13/0001* (2013.01); *A61C 13/0019* (2013.01); *A61C 13/34* (2013.01); *A61C 8/005* (2013.01); *A61C 8/0048* (2013.01); *A61C 8/0095* (2013.01)

(58) Field of Classification Search
CPC ....... A61C 8/0089; A61C 8/001; A61C 1/082; A61C 1/084; A61C 13/0001; A61C 13/0019; A61C 13/34; A61B 6/14; A61B 17/176
See application file for complete search history.

(56) References Cited

U.S. PATENT DOCUMENTS

| | | | |
|---|---|---|---|
| 5,725,376 A | 3/1998 | Poirier | |
| 6,382,975 B1 | 5/2002 | Poirier | |
| 6,814,575 B2 | 11/2004 | Poirier | |
| 6,997,707 B2 | 2/2006 | Germanier | |
| 7,331,786 B2 | 5/2008 | Poirier | |

(Continued)

FOREIGN PATENT DOCUMENTS

| | | |
|---|---|---|
| CN | 203988446 | 12/2014 |
| MX | 2014001163 | 7/2015 |

(Continued)

*Primary Examiner* — Heidi M Eide
(74) *Attorney, Agent, or Firm* — David L. King

(57) ABSTRACT

A dental alignment guide system for dental implant placement has an anatomical guide, a tooth supported guide and a surgical guide. The system further can have an articulation piece, a prosthetic seat, an analog anatomical model and artificial teeth. The system has a plurality of implants, the implants being abutments, preferably multiunit abutments, a plurality of screws for attaching the anatomical guide to bone, pins to removably attach the various guides and the artificial teeth to the anatomical guide as assemblies during the method of practicing the invention.

26 Claims, 27 Drawing Sheets
(13 of 27 Drawing Sheet(s) Filed in Color)

(56) References Cited

U.S. PATENT DOCUMENTS

| | | |
|---|---|---|
| 7,758,345 B1 * | 7/2010 | Christensen ............ A61C 9/00 |
| | | 433/214 |
| 7,866,980 B2 | 1/2011 | Poirier |
| 7,905,726 B2 | 3/2011 | Stumpel |
| 7,950,924 B2 | 5/2011 | Brajnovic |
| 8,021,153 B2 | 9/2011 | Poirier |
| 8,142,189 B2 | 3/2012 | Brajnovic |
| 8,186,999 B2 | 5/2012 | Andersson et al. |
| 8,535,055 B2 | 9/2013 | Katz |
| 9,504,533 B2 | 11/2016 | Groscurth et al. |
| 9,795,458 B2 | 10/2017 | Llop |
| 2008/0038692 A1 | 2/2008 | Andersson et al. |
| 2009/0011382 A1 * | 1/2009 | Bavar .................... A61C 1/084 |
| | | 433/76 |
| 2014/0272778 A1 | 9/2014 | Llop |
| 2015/0010881 A1 | 1/2015 | Llop |
| 2015/0272704 A1 | 10/2015 | Watson et al. |
| 2015/0272705 A1 | 10/2015 | Watson et al. |
| 2015/0359479 A1 | 12/2015 | Crandall et al. |
| 2016/0038255 A1 | 2/2016 | Llop |
| 2016/0157967 A1 * | 6/2016 | Kim ........................ A61C 5/70 |
| | | 433/201.1 |
| 2016/0278878 A1 | 9/2016 | Watson et al. |
| 2017/0071697 A1 | 3/2017 | Groscurth et al. |
| 2017/0112591 A1 | 4/2017 | Llop |
| 2017/0112592 A1 * | 4/2017 | Groscurth .......... A61C 13/0004 |
| 2017/0165030 A1 | 6/2017 | Liu |
| 2017/0252126 A1 * | 9/2017 | Llop ................... A61C 8/0092 |
| 2017/0281307 A9 | 10/2017 | Llop |
| 2018/0333229 A1 * | 11/2018 | Watson ................ A61C 8/0053 |

FOREIGN PATENT DOCUMENTS

| | | |
|---|---|---|
| WO | 2017171320 | 10/2017 |
| WO | 2017203419 | 11/2017 |

* cited by examiner

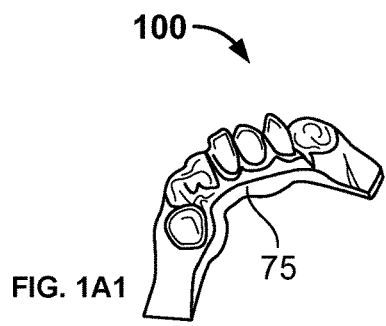
FIG. 1A1
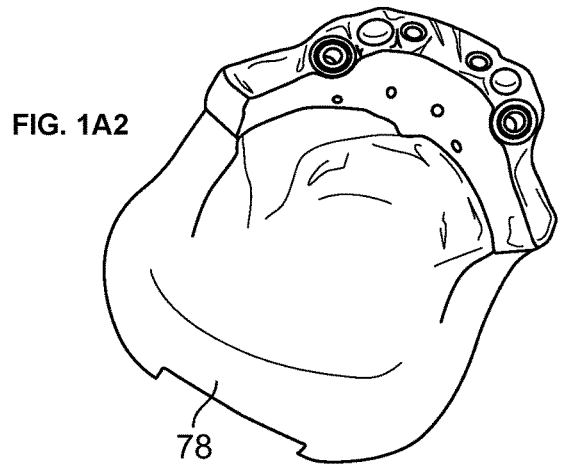
FIG. 1A2
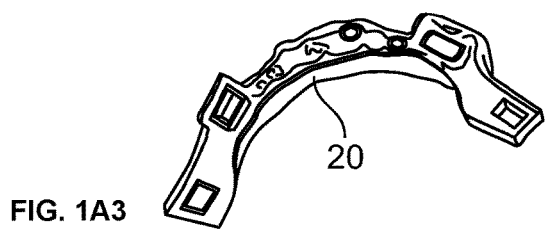
FIG. 1A3
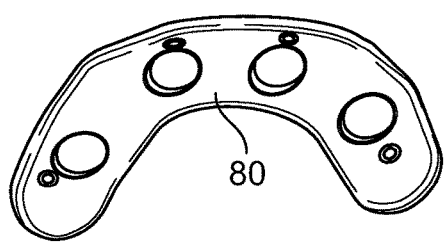
FIG. 1A4
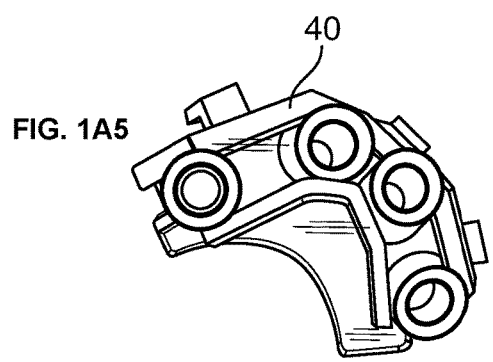
FIG. 1A5
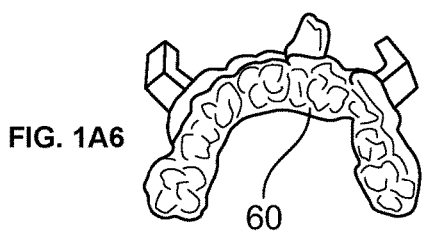
FIG. 1A6
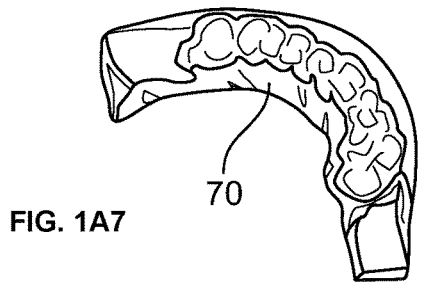
FIG. 1A7
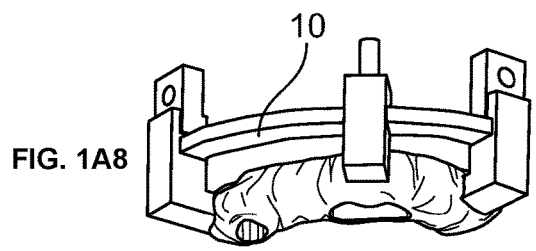
FIG. 1A8

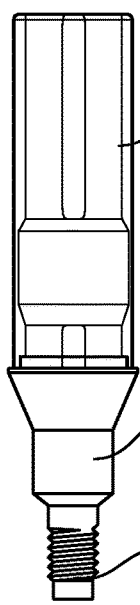
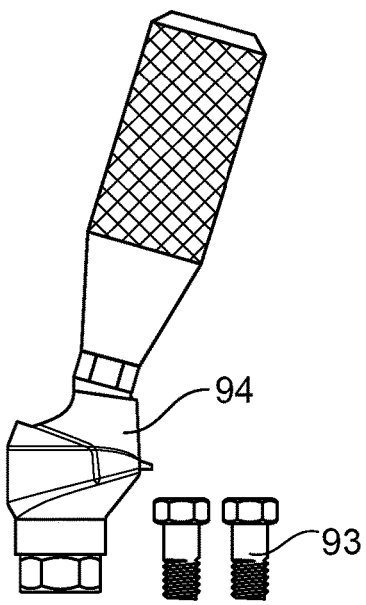
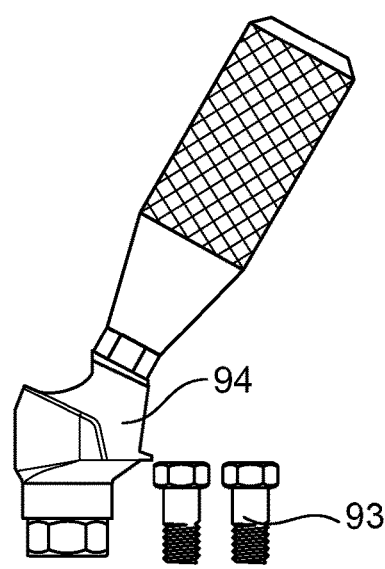
FIG. 1C1  FIG. 1C2  FIG. 1C3

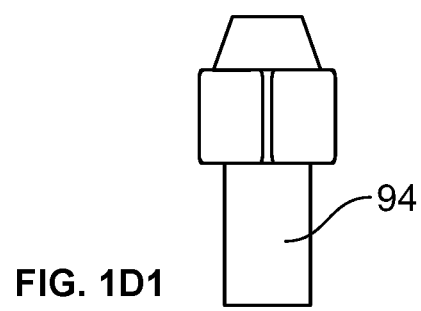
FIG. 1D1
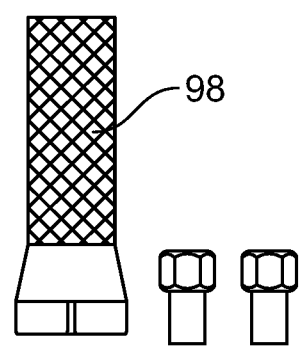
FIG. 1D2

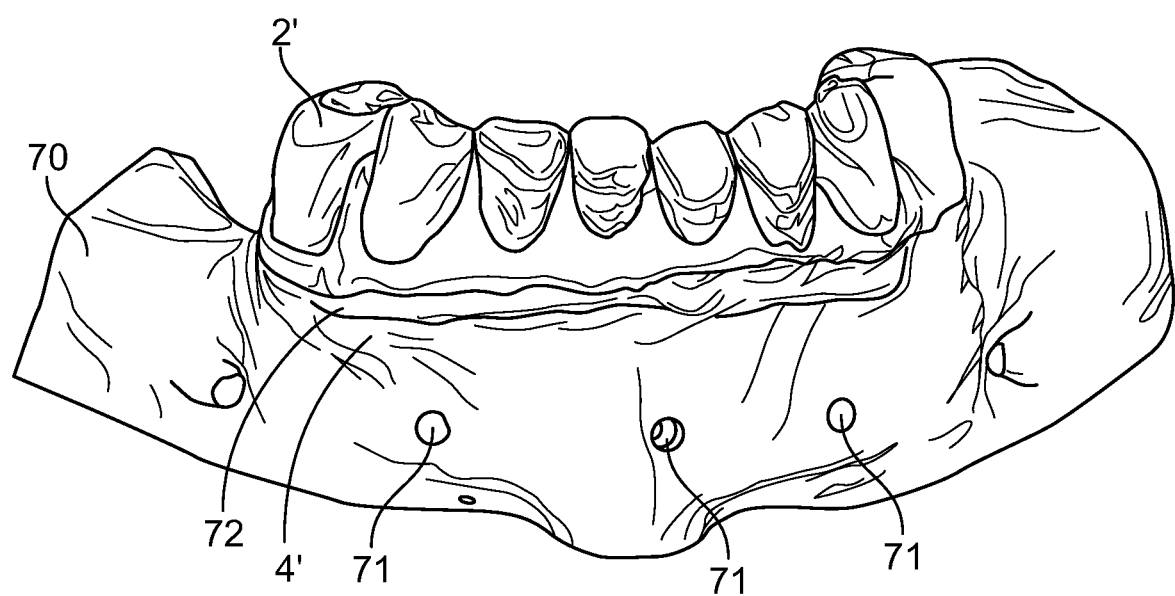
FIG. 3A

DENTAL ALIGNMENT SYSTEM AND METHOD FOR DENTAL IMPLANT PLACEMENT

TECHNICAL FIELD

An improved dental alignment guide method and system for dental implant placement is disclosed.

BACKGROUND OF THE INVENTION

A variety of surgical guide devices are being used to assist in the placement of dental implants.

These guides are commonly divided into three classes, bone borne surgical drill guides and gum tissue borne surgical guides that are used in full arch cases and tooth borne guides that are typically used in partial arch cases. The tooth borne guide works well for smaller arch cases requiring two or three implants, but doesn't work well for full arch cases as the teeth must be removed.

In bone borne guides, the soft gum tissue is removed or at least displaced by flapping to expose the patient's jaw bone. The bone borne surgical guides is made to fit on the bone and is made from digital jawbone model or by rapid prototype models made by 3D printing.

Gum tissue borne surgical guides fit directly onto the soft gum tissue. It is a less invasive technique, but it is generally considered inferior to bone borne guides as the soft tissue is generally unstable and, therefore the ability to maintain alignment and accuracy is sacrificed.

Both of these current forms of guides have drawbacks, one of which is the bulky size and structure of the guides which occupy a large amount of space in the patient's mouth. Often, the pins and fasteners used to secure the guide protrude and project into the patient's soft facial tissue. In the prior art the devices rely on seating on the ridge of the bone. this is highly inaccurate due to the inability to determine bone in the area of the ridge and tooth extraction. This area changes during extraction as well creating more inaccuracy. The present invention now seats on the facial bone that is much clearer in the CT images. This allows the guide to be inserted from the facial direction onto the buccal or labial bone. The placement of the guide on the buccal bone is more accurate than previous designs that are pinned 10-15 mm from implant placement. The present invention is can be within 2 to 3 mm from implant placement.

Another drawback is the time required to prepare large areas of exposed bone on both the labial and the lingual side, in the case of bone supported guides, wherein the creation of the large flap is painful when the patient comes out of sedation and also increases the risk of infection. This length of time of surgery is problematic as the patient is under sedation and therefore exposed to higher risk.

The present invention, unlike the prior art devices which have bulky structures straddling both sides of the jaw bone for support, is greatly reduced in size and yet is accurately secured to bone.

The present invention provides a system that is extremely accurate and precise while much quicker and easier to use, thus reducing the time of the surgical procedure.

The system of the present invention as described herein provides a plurality of devices that aid the surgeon and allow for an improved patient outcome.

SUMMARY OF THE INVENTION

A dental alignment guide system for dental implant placement has an anatomical guide, a tooth supported guide and a surgical guide. The system further can have an articulation piece, a prosthetic seat, an analog anatomical model and artificial teeth. The system has a plurality of implants, abutments, preferably multiunit abutments, titanium cylinders and a plurality of screws for attaching the anatomical guide to bone, pins to removably attach the various guides and the artificial teeth to the anatomical guide as assemblies during the method of practicing the invention.

The anatomical guide has an arch shaped structure having a first end and a second end. The arch shaped structure has a curved exterior wall and a curved interior wall extending between the ends. The interior wall is formed using a 3D scan of a patient to mimic bone without any gum tissue and configured to abut directly against and be secured to a portion of a labial and/or buccal side of a patient's exposed bone of the alveolar process with soft gum tissue removed or displaced by flapping. The curved exterior wall has at least one fastener opening extending through the arch shaped structure. Each fastener opening is configured to receive a fastener to secure the anatomical guide to the exposed bone of either the mandible or the maxilla, preferably the fasteners are threaded screws. The tooth supported guide is made with a curved structure configured to vertically fit onto a patient's existing teeth and connects to the anatomical guide with a latch which includes a connection extending from the curved structure to an end. The connection is sized to be received and complimentarily fit into a connection aperture on the anatomical guide. The anatomical guide and the tooth supported guide when connected together at the latch form an assembly. The assembly of the anatomical guide and the tooth supported guide are tooth supported vertically to align the interior wall of the anatomical guide to abut against the exposed bone prior to securing the anatomical guide with fasteners to the exposed bone. Alternatively, the anatomical guide can be seated against the bone in the correct position based on the anatomy. Then the tooth supported guide can be inserted over the teeth and assembled to the anatomical guide verifying correct placement. The assembly is configured to pivot or rotate as the tooth supported guide is placed onto the teeth while sliding into place allowing the attached anatomical guide to pass under the teeth to abut against the exposed bone while being partially under an undercut of the exposed bone and teeth. The connection can be a plurality of support bars extending from the curved structure to an end. Each end of the support bars is sized to be received and complimentarily fit into a connection aperture of the latch on the anatomical guide. At least the ends of the support bars of the tooth supported guide in proximity to one of the first end and the second end of the anatomical guide have an opening and the connection aperture of the anatomical guide has a pair of openings aligned with said support bar end opening on assembly. The aligned openings are configured to receive a pin or locking device for supporting and coupling the anatomical guide to the tooth supported guide. The tooth supported guide has at least one leg support. In one embodiment the tooth supported guide has three leg supports, a middle leg support interposed between the other two leg supports, the middle leg support can have an end with a round cross section, the other two leg supports having the ends with either a polygonal cross section having three or more sides or a circular cross-section or any combination thereof. The curved structure has a plurality of apertures on the curved structure, the apertures forming windows open to verify tooth position. The tooth supported guide has a support structure spanning between and connecting each pair of adjacent support bars, the support bars being below the curved structure and above the ends of the support bars. The tooth supported guide is removably latch to the anatomical guide as the assembly, and the anatomical guide after being fastened to the exposed bone can have the tooth supported guide removed from the assembly. The dental alignment guide system further has at least one threaded screw to fasten the anatomical guide to the exposed bone. Each of the at least one screw passing through one of the at least one fastener openings of the anatomical guide. The anatomical guide has a flat outer surface extending between the curved interior wall and the curved exterior wall to provide a bone cutting guide surface to cut through the bone and optionally the teeth to create a reduced bone with teeth removed to receive implants. The anatomical guide has a cross-sectional thickness along the arch shaped structure to prevent buckling between the opposing interior wall and exterior wall. The dental alignment guide system further has a surgical guide. The surgical guide is made with a curved structure having a connection. The curved structure has a plurality of openings extending from an outer surface toward a reduced bone surface of the alveolar process. The openings are configured to receive implants or drills for guiding the drills and implants through the surgical guide as planned. The connection extends from the curved structure to an end. The connection is sized to be received and complimentarily fit into a connection aperture of the latch on the anatomical guide and thereafter supported on the pins. The anatomical guide and the surgical guide when connected together form an assembly. The connection of the surgical guide is dimensionally the same as the connection of the tooth guide to fit the connection aperture of the anatomical guide. The surgical guide has an exposed outer surface with a plurality of implant openings each implant opening being a guide tube. Each guide tube is positioned in one of the plurality of implant openings to direct a placement of a drill and an implant into the reduced bone. The surgical guide further has an analog model replicating the patient's reduced bone with implant placements. The analog model has a pair of attachment openings configured to receive an articulation piece. The dental alignment guide system further has an articulation piece. The articulation piece has a pair of attachment posts for attachment into the pair of attachment openings on the surgical guide. The articulation piece replicates the patient's teeth and bone that existed prior to a bone reduction to provide for alignment and articulation. The dental alignment guide system further has a prosthetic seat with openings aligned with the implant openings, the prosthetic seat being positioned on the reduced bone with identifying markers for abutment pieces to be attached to the implants in the reduced bone between the reduced bone and the artificial teeth. The dental alignment guide system further has an anatomical model of the patient's teeth and exposed alveolar process with soft tissue removed to replicate the patient's teeth and mandible or maxilla prior to any teeth extraction or bone reduction. The anatomical model is a three-dimensional model made by combining laser scanning of the patient's teeth with a CT image of the patient's anatomy and 3D printing. The dental alignment guide system further has a plurality of implants. The implants are configured to pass through the guide tubes of the surgical guide. The implants are driven into the reduced bone while being guided by the guide tube securely fixed to the bone at a desired angle, depth and rotation. The rotation is controlled by aligning markers on the implant driver to markers on the surgical guide at a depth stop. The system further has abutments for attachment to the implants. Each abutment has one or more alignment flats or slots and the prosthetic seat is marked to indicate an alignment location for the flats or slots to control rotation to a desired angle. Each abutment has internal threads. Each abutment has an exposed end configured to receive and temporarily hold a cylinder, each cylinder being pre-cut to a desired length. The dental alignment guide system further has prosthetic artificial teeth. The artificial teeth have a connection configured to align with the connection aperture of the anatomical guide to form an assembly. The prosthetic artificial teeth have a plurality of holes configured to align with the cylinders attached to the abutments and to receive the cylinders into the holes at the desired length so the cylinder end is at or below the surface of the teeth when the artificial teeth are attached to the anatomical guide. The dental alignment guide system further has a plurality of straws. A straw is inserted into an open end of the cylinder to occlude the opening to the screw access to prevent occlusion of the access when a light or self-curing material is applied to the holes of the artificial teeth to bond and secure the cylinders to the artificial teeth. The artificial teeth are removed from the anatomical guide with the cylinders fixed to the artificial teeth. The connection is removed and the artificial teeth are polished and prepared for placement into the patient. The anatomical guide is unfastened from the bone and the soft tissue flap sutured prior to attaching the artificial teeth. A plurality of screws are configured to pass through the cylinders and thread into the abutments thereby securing the artificial teeth to the reduced bone.

In one embodiment, the anatomical guide has a nasal vertical mount portion integrally formed or otherwise affixed to an opposing outer surface relative to the flat outer surface. The nasal vertical mount portion extends from the anatomical guide to buttress against cheek bones. The portion has nasal clips configured to assist in vertically positioning the anatomical guide interior surface against the exposed bone of the maxilla. In the preferred embodiment, each nasal clip has an aperture.

Definitions

The alveolar process (alveolar bone) is the thickened ridge of bone that contains the tooth sockets (dental alveoli) on bones that hold teeth. In humans, the tooth-bearing bones are the maxillae and the mandible.

Anterior—The direction towards the front of the head or the lips, as opposed to posterior, which refers to the directions towards the back of an individual's head. The term anterior teeth refers to incisors and canines, as opposed to premolars and molars, which are posterior teeth.

Apical—The direction towards the root tip(s) or apex(es) of a tooth (the apices), as opposed to coronal, which refers to the direction towards the crown. It may also refer to something relating to the roots, such as apical support. When referring to direction in relation to entities on or of the crown, this term can be synonymous with both cervical and gingival.

Axial—A plane parallel to the surface of a tooth. For example, if a drill bur would be inserted into a tooth from any side (proximal, vestibular, oral), the depth of the hole is defined from the axial wall of the hole (from the long axis walls (vertical surfaces bounding the tooth)).

Buccal—The side of a tooth that is adjacent to (or the direction towards) the inside of the cheek, as opposed to lingual or palatal (both oral), which refer to the side of a tooth adjacent to (or the direction towards) the tongue or palate, respectively, the oral cavity. Although technically referring only to posterior teeth (where the cheeks are present instead of lips, use of this term has incorrectly extended to all teeth, anterior and posterior), this term has inaccurately been employed to describe the vestibular surface of (or directions in relation to) anterior teeth as well.

Cervical—Means neck in Latin (as in cervical vertebrae), and refers to the narrowing of the contours of the tooth surface at or near the CEJ, where the crown meets the root. When referring to direction in relation to entities on or of the crown, it is nearly synonymous with both apical and gingival.

Coronal—The direction towards the crown of a tooth, as opposed to apical, which refers to the direction towards the tip(s) of the root(s) or apex(es). It may also refer to something relating to the crown, such as coronal forces.

Distal—The direction towards the gingiva beyond the tooth furthest from the anterior midline (the 'most posterior tooth' or last tooth) in each quadrant of a dental arch, as opposed to mesial, which refers to the direction towards the anterior midline. Each tooth can be described as having a distal surface and, for posterior teeth, a distobuccal (DB) and a distolingual (DL) corner or cusp.

Facial—The side of a tooth that is adjacent to (or the direction towards) the inside of the lips, as opposed to lingual or palatal (both oral), which refer to the side of a tooth adjacent to (or the direction towards) the tongue or palate, respectively, the oral cavity. However, this term has been incorrectly used as an umbrella term for both the term buccal and labial, being also applied to the side of a tooth that is adjacent to (or the direction towards) the inside of the cheek (instead of the more accurate term, vestibular).

Gingival—The direction towards the gingiva (gums), synonymous with cervical and similar to apical. However, locations on teeth already more apical to the interface of the crown and root, referred to as the CEJ, tend not to be described using this term, as it would lead to confusion, as the exact definition is ambiguous. Additionally, this term would not be used when referring to a tooth ex vivo.

Incisal—The direction towards the biting edge of anterior teeth or something relating to this edge, such as the terms incisal guidance or incisal edge. This is the sister term to occlusal, which related to the analogous location on posterior teeth.

Inferior—The direction towards the feet of a human's body, as opposed to superior, which refers to the direction towards the head. However, use of these terms should enjoy only limited usage when discussing features of a tooth, as, for example, something more inferior on a mandibular tooth will be situated more superior on a maxillary tooth, as they exhibit an inverted relationship. It is for this reason that the terms coronal and apical are substituted.

Interproximal—An adjective meaning between teeth. For example, interproximal teeth refers to the space between adjacent teeth.

Labial—The side of a tooth that is adjacent to (or the direction towards) the inside of the lip (labium), as opposed to lingual or palatal (both oral), which refer to the side of a tooth adjacent to (or the direction towards) the tongue or palate, respectively, the oral cavity. Although technically referring only to anterior teeth (where the lips (labia) are present instead of cheeks), use of the term buccal has inaccurately extended to all teeth, anterior and posterior (instead of vestibular, the umbrella term).

Lingual—The side of a tooth adjacent to (or the direction towards) the tongue (*lingua*, compare linguistics and language), as opposed to buccal, labial, or vestibular which refer to the side of a tooth adjacent to (or the direction towards) the inside of the cheek or lips, respectively. Although this term is technically specific to the mandible, it enjoys extensive use in reference to the maxilla as well (see Palatal).

Mandibular Entities related to the mandible, or lower jaw.

Marginal—A number of different 'margins' that are involved in dentistry. The edge of tooth structure that is prepared to meet the edge of a prosthetic crown is called a margin, as is the aforementioned edge of the crown; an example of this usage would be "a poorly fitting crown might exhibit marginal leakage." The gingiva and bone that abut the teeth are referred to as 'marginal', as in marginal periodontitis. The bulk of tooth structure on the occlusal surface at the point of contact of posterior teeth is referred to as the marginal ridge.

Maxillary Entities related to the maxilla, or upper jaw.

Mesial—The direction towards the anterior midline in a dental arch, as opposed to distal, which refers to the direction towards the gingiva beyond the tooth furthest from the anterior midline (the 'most posterior tooth' or last tooth) in each quadrant. Each tooth can be described as having a mesial surface and, for posterior teeth, a mesiobuccal (MB) and a mesiolingual (ML) corner or cusp.

Midline—Main article: Dental midline. Roughly, an imaginary vertical line dividing the left and right sides of the mouth at the teeth.

Occlusal—The direction towards the biting surface of posterior teeth or something relating to this surface, such as the terms occlusal interference or occlusal surface. This is the sister term to incisal, which related to the analogous location on anterior teeth.

Oral—The side of a tooth adjacent to (or the direction towards) the oral cavity, as opposed to buccal, labial or vestibular, which refer to the side of a tooth adjacent to (or the direction towards) the inside of the cheek, lips or vestibule respectively. This term is an umbrella term for both the term palatal and lingual. Alternatively, the term lingual has been used as a blanket term instead although this specifically refers only to the side of a tooth that is adjacent to (or the direction towards) the tongue, technically specific to the mandible.

Palatal—The side of a tooth adjacent to (or the direction towards) the palate, as opposed to buccal, labial or vestibular which refer to the side of a tooth adjacent to (or the direction towards) the inside of the cheek, lips and vestibule of the mouth respectively. This term is strictly used in the maxilla.

Posterior—The direction towards the back of an individual's head, as opposed to anterior, which refers to the directions towards an individual's lips. The term posterior teeth refers to premolars and molars, as opposed to incisors and canines, which are anterior teeth.

Proximal—The surfaces of teeth that normally lie adjacent to another tooth. It is an umbrella term that includes both mesial and distal, such as when referring to the proximal surfaces of teeth.

Dental quadrants—The dentition is divided into four quarters. The two dental arches form an oval, which is divided into quadrants: Upper right quadrant: upper right first incisor to upper right wisdom tooth. Upper left quadrant: upper left first incisor to upper left wisdom tooth. Lower right quadrant: lower right first incisor to lower right wisdom tooth. Lower left quadrant: lower left first incisor to lower left wisdom tooth. Sextant—One of six groups of adjacent teeth, excluding the wisdom teeth. The front sextants go from canine to canine, and there are sextants on the right and left of these.

Superior—The direction towards the head of a human's body, as opposed to inferior, which refers to the direction towards the feet. However, use of these terms should enjoy only limited use when discussing features of a tooth, as, for example, something more superior on a mandibular tooth will be situated more inferior on a maxillary tooth, as they exhibit an inverted relationship. It is for this reason that the terms coronal and apical are substituted.

Vestibular—The side of a tooth that is adjacent to (or the direction towards) the inside of the cheeks and lips, as opposed to lingual or palatal (both oral), which refer to the side of a tooth adjacent to (or the direction towards) the tongue or palate, respectively, the oral cavity. This term is an umbrella term for both the term buccal and labial. Alternatively, the term facial has been used as the umbrella term instead although this specifically refers only to the side of a tooth that is adjacent to (or the direction towards) the inside of the lips, as opposed to lingual or palatal (both oral), and not the cheeks.

Zygoma implants (or Zygomatic implants) are different from conventional dental implants in that they anchor in to the zygomatic bone (cheek bone) rather than the maxilla (upper jaw). They may be used when maxillary bone quality or quantity is inadequate for the placement of regular dental implants.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

The invention will be described by way of example and with reference to the accompanying drawings in which:

FIGS. 1A1-1A8 are views of the various components of the dental alignment system of the present invention.

FIGS. 1C1-1C3 are views of exemplary abutments.

FIGS. 1D1 and 1D2 are views of various implant parts and abutments.

FIG. 2 is a frontal perspective view of the anatomical guide of the present invention.

FIG. 3A is a frontal perspective view of an anatomical model of an exemplary patient's teeth and bone with the soft gum tissue removed.

FIG. 8 is a view of the articulation piece shown assembled to the analog model.

DETAILED DESCRIPTION OF THE INVENTION

Figure 13:
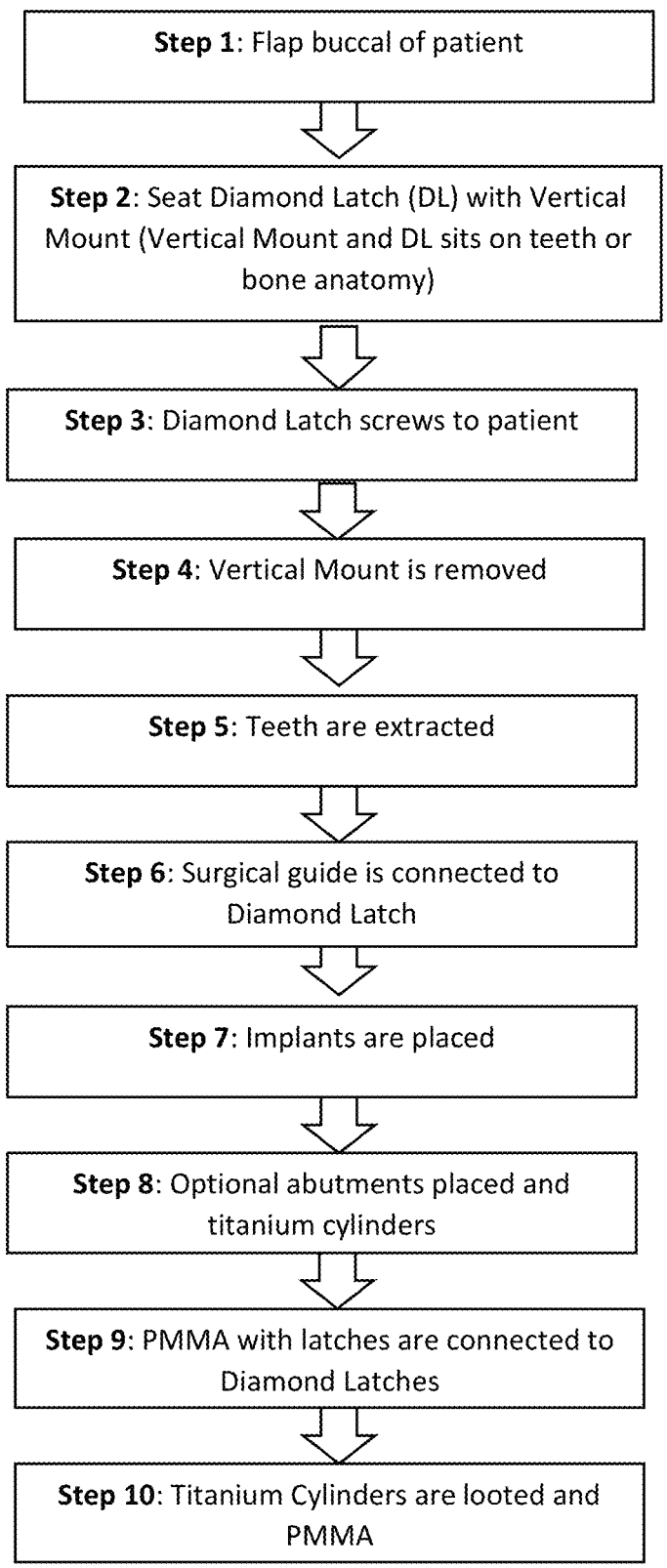
FIG. 13 is a schematic diagram of the method of the present invention.

With reference to the following drawings represented in FIGS. 1A1-12, a plurality of devices that make up the dental alignment guide system 100 of the present invention are shown. With reference to FIG. 13, a diametric schematic plan illustrates how the dental alignment guide system is used in preparing and implanting a dental implant into a patient. With reference to FIGS. 14-39, an exemplary procedure of a dental implant being placed into a patient utilizing the dental alignment guide system 100 of the present invention is illustrated showing the techniques and methods used in utilizing the dental alignment guide system of the present invention.

The present invention affords an opportunity to enable a surgeon to quickly accurately and very precisely implant artificial teeth into a patient with a minimum amount of time under sedation with the opportunity to provide adequate cooling of the underlying bone structure to insure there is no bone degradation during the procedure. These benefits will be described in conjunction with the various devices that are used in the alignment system. The system 100 shown in FIGS. 1A1-1A8 and 1E, can be considered a kit composed of a variety of components, some of the components being manufactured using rapid printing or 3D printing technology and additive building using computer software that will mimic and accurately profile the devices to complimentarily match the patient's existing teeth in many cases or exposed bone of either the mandible or the maxilla providing a secure anatomical guide system to allow bone reduction to occur in a very precise manner so that when implants are placed to attach artificial teeth to the bone structure and secured thereto, the implant will have a very refined alignment such that the implanted artificial teeth will fit precisely in the patients mouth.

Figure 1B:
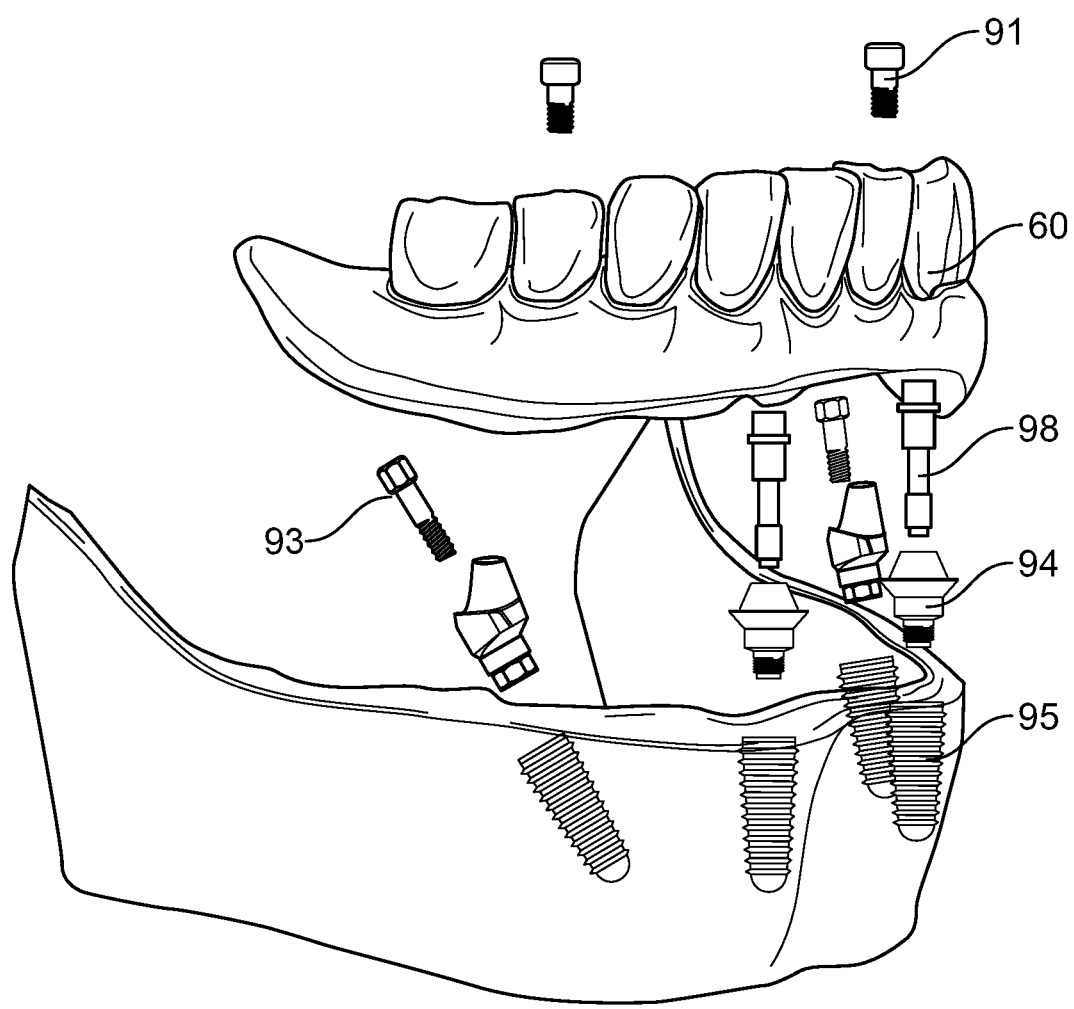
FIG. 1B is a perspective view of the abutments and fasteners used to secure an exemplary set of artificial teeth.
Figure 1E:
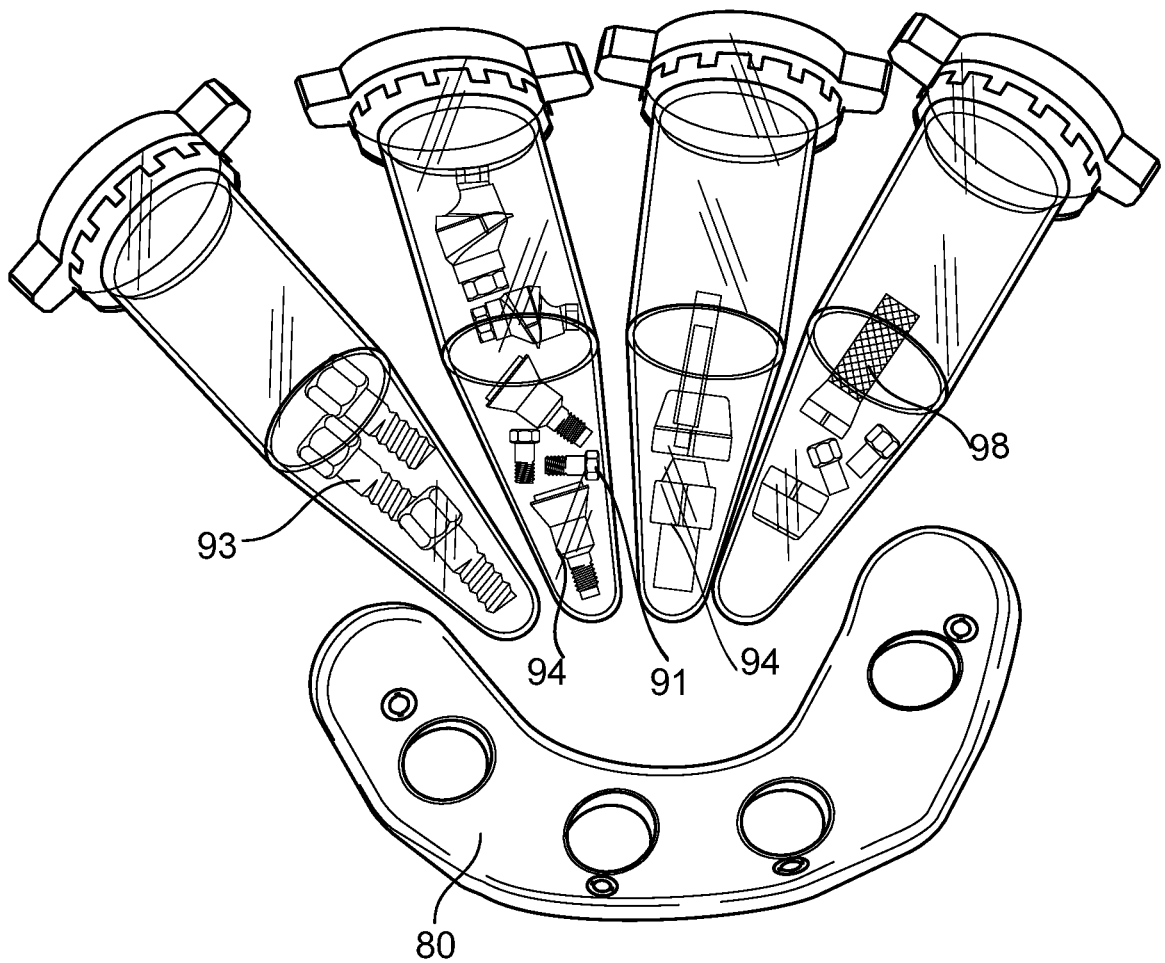
FIG. 1E is a perspective view of the various fasteners used with the system and the prosthetic seat.
Figure 1F:
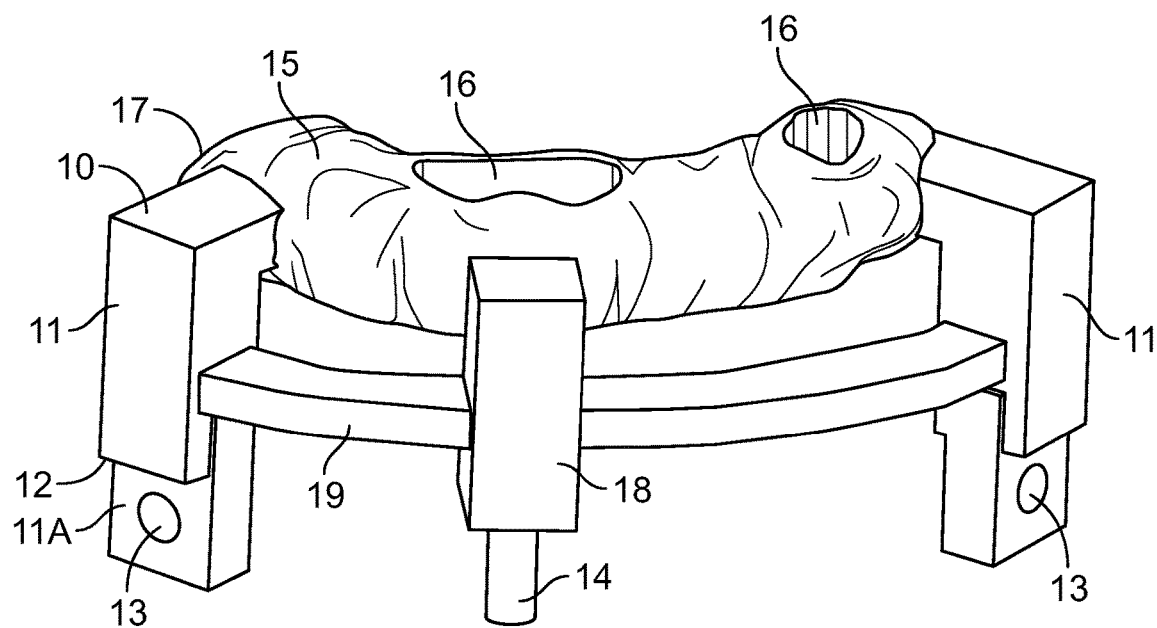
FIG. 1F is a frontal perspective view of a tooth supported guide of the present invention.

With reference to FIG. 1F, a tooth supported guide 10 or also referred to as a tooth vertical mount is shown. The tooth supported guide 10 is illustrated has an arch shaped structure with an internal cavity 17 that replicates the patients existing teeth. On the outer surface of the curved "U" shaped structure are a plurality of windows or holes 16 that allow the tooth supported guide 10 to be checked and verified for proper placement when positioned over a patient's existing teeth. As illustrated, the tooth supported guide 10 is for the lower teeth secured to the mandible or the alveolar process of the patient. Extending outward in a forward direction form the "U" shaped structure is a connection 11, the connection 11 is at least one support bar 11 as shown, there are a plurality of support bars 11. Each support bar 11 extends to an end, the curved structure has a first end and a second end. In proximity to each end is one support bar 11. As shown in FIG. 1, the support bars 11 in proximity to the ends have a shape that has a lower end that is of a polygonal cross section having three or more sides, as shown square or rectangular. Alternatively, a circular cross-section or any combination thereof can be used. Each of these support bars 11 at the ends has a through hole 13, this through hole 13 is for alignment purposes and most importantly for support. Interposed between the two support bars 11 in proximity to the first and second end is a middle support bar 18. The middle support bar 18 in the middle location has a circular or round cross-sectional peg or pin 14. Spanning between each support bar 11, 18 is a support structure 19 connecting each support bar 11, 18 and providing additional rigidity between the support bars at a location between the top and the bottom of each support bar 11, 18. As shown, each support bar has an enlarged section 12 directly above the end. These enlarged sections 12 provide stops.

Figure 2:
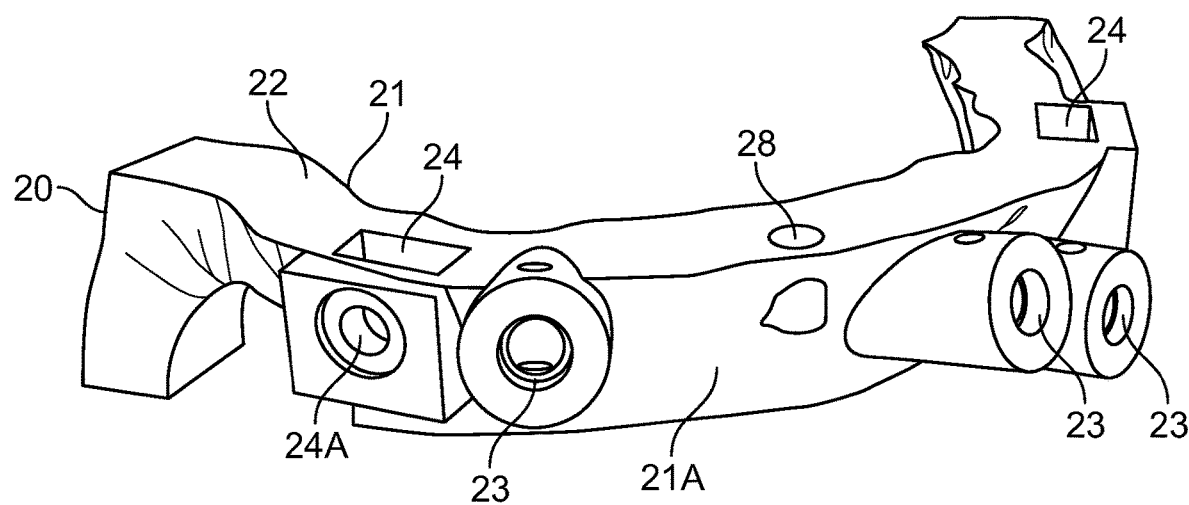
Figure 4A:
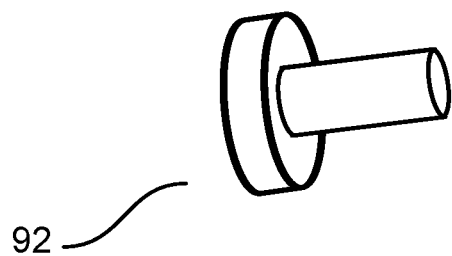
FIG. 4A is a perspective view of the support pin of the latch.
Figure 4B:
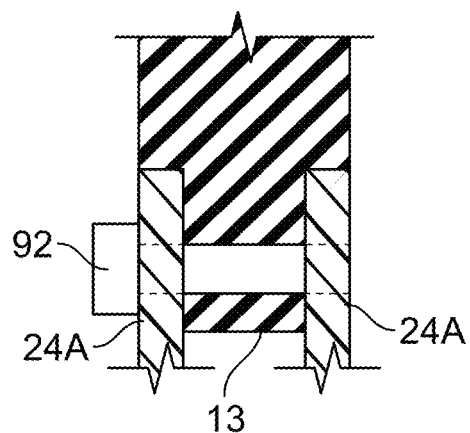
FIG. 4B is a cross sectional view of the latch system of the present invention.

With reference to FIG. 2, an anatomical guide 20 is illustrated. The anatomical guide 20 as shown is a curved arch with an interior wall 21 and an exterior wall 21A. The distance between walls provides a thickness, as shown the anatomical guide 20 typically has a thickness of approximately 6 mm. This is substantially thicker than most other guides. Interestingly, the interior wall 21 is designed using a 3D scan of the patient to directly mimic the bone of the patient. The patient's teeth and bone having been previously scanned allows the software to predict the bone surface when the gum tissue has been flapped or displaced. As such the anatomical guide 20 will fit precisely against the bone in the absence of the gum tissue. The top surface 22 between the interior wall 21 and the exterior wall 21A creates a flat surface 22 that will facilitate the surgeon in making a bone reduction when the anatomical guide 20 is secured tightly to the patient's alveolar process. The anatomical guide 20 has at least one opening 23 for receiving a fastener to secure the guide 20 to the exposed bone. As illustrated, there are a plurality of fastener openings 23. The fastener openings 23 are provided to secure the anatomical guide 20 to the patient's bone using threaded fasteners or screws. Additionally, at least one connection aperture 24 is provided to receive a connection from the tooth supported guide 10, as shown, there are a plurality of apertures 24. One connection aperture 24 is near a first end and a second connection aperture 24 is in proximity to a second end with a middle connection aperture 28 that is of a round cross section shown interposed between the first two apertures. As previously discussed, the tooth supported guide 10 or vertical tooth mount can be assembled wherein the support bars 11, 18 are pushed onto and into the connection apertures 24 of the anatomical guide 20. When this occurs, the connection apertures 24 have holes 24A that align with the holes 13 at the ends of the support bars 11 to receive the support pins 92 as shown in FIGS. 4A and 4B to support the tooth supported guide 10. When the assembly of the tooth supported guide 10 and the anatomical guide 20 is made, pins 92, shown in FIG. 1E, can be positioned in the support bar holes 13 and connection aperture holes 24A securing the assembly.

Figure 3B:
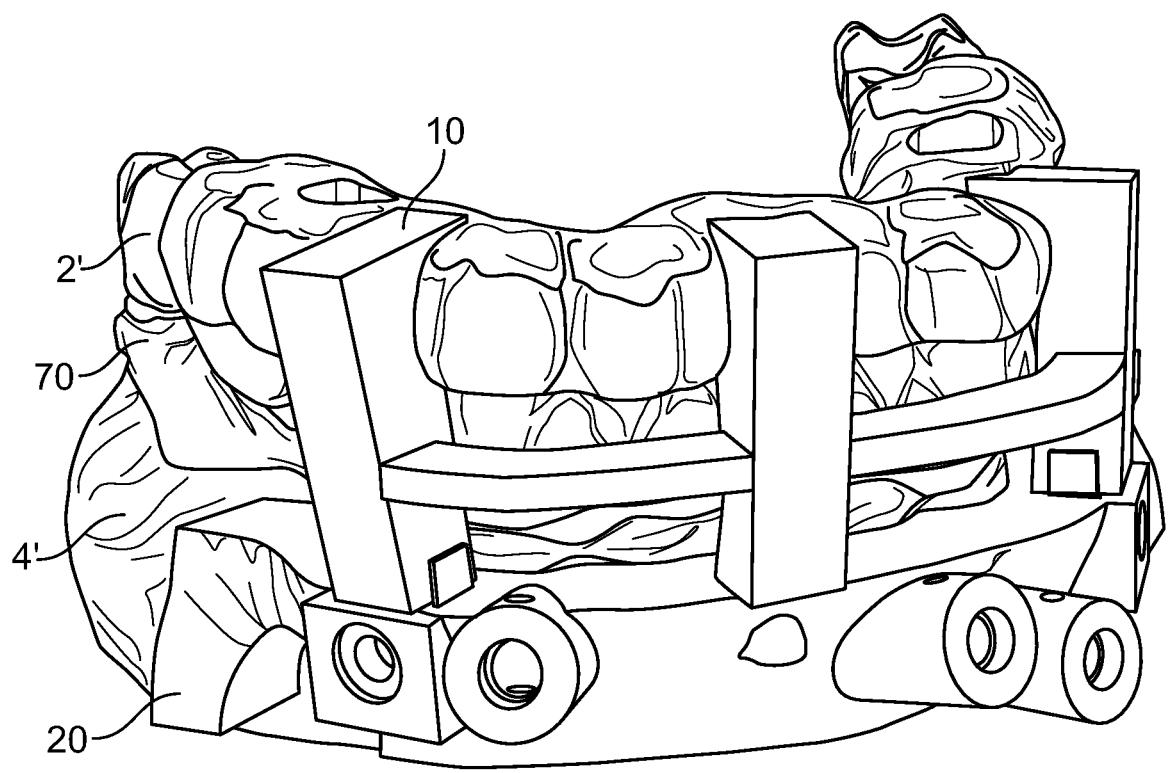
FIG. 3B is a frontal perspective view of the tooth supported guide inserted into the anatomical guide to form an assembly, the assembly, as illustrated, being placed on the anatomical model of FIG. 3A.

With reference to FIG. 3A, a model 70 of the patient's bone and existing teeth with the gum flap removed is made by a 3D image that exactly replicates this structure. This provides the surgeon with an opportunity to place the assembled tooth supported guide 10 and anatomical guide 20 as an assembly over the replicated bone 4' and teeth 2' model 70 to insure proper alignment and fit. As shown, the patient's bone and scan of teeth of the model 70 has a plurality of holes 71 that allow the surgeon to fasten the anatomical guide 20 directly to the portion replicating the exposed bone. This is the exact procedure that will be replicated when doing a surgery on a patient's failing teeth. As shown, in the patient bone and laser scanned teeth model 70, there is a ridge 72 between the teeth 2' and the bone 4' and it is important that the assembly of the tooth supported guide 10 and anatomical guide 20 are able to pass over the teeth 2 in such a way that the anatomical guide 20 at the interior wall 21 is positioned below this ridge 72. In order to accomplish that, the internal cavity 17 of the tooth supported guide 10 is such that it can be tilted at a slight angle outward or proximally so that as the surgeon is placing the assembly over the teeth 2, the tooth supported guide 10 will slide down and over the teeth 2 while projecting slightly outwardly. As this is occurring, the entire assembly will pivot while rotating down so that the interior wall 21 of the anatomical guide 20 passes over this ridge 72 and lies directly under it, as illustrated in FIG. 3B.

With reference to FIG. 3B, the assembly of the tooth supported guide 10 and the anatomical guide 20 is shown placed over the model 70 of a patient's bone 4' and scan of the teeth 2'. When this occurs, the interior wall 21 which exactly replicates the bone structure 4, will sit very flush and precisely against the bone structure 4, the surgeon will then look at the patient and determine whether or not the fastener holes 23 are free of any obstructing tooth roots. If a tooth 2 is in the way, the surgeon will remove the entire assembly 10, 20 and extract any teeth 2 that are interfering with any fasteners 90. Then the surgeon will place the assembly back over the teeth 2 and fasten the screws or fasteners 90 in place. In addition, the holes 13, 24A provided for alignment will be filled with a pin 92, illustrated in FIG. 4A, and shown later in a discussion of an actual procedure. These alignment pins 92 extend through the anatomical guide 20, through the hole 13 in the support bar 11 end and reenter a hole 24A on the interior wall 21 such that the tooth supported guide 10 is securely fastened to the anatomical guide 20 prior to fastening the anatomical guide 20 to the bone 4. The anatomical guide 20 can be provided with optional metal sleeves 23A that will be illustrated in later views on an existing patient. These sleeves 23A, if used, provide a reinforcement of the fastening openings 23. When a fastener 90 is inserted into the anatomical guide 20, it is preferably a threaded screw 90 that fits flush against the fastener opening 23. This allows for a tight fit with minimal obstruction in the patient's mouth. As noted, the arch shaped anatomical guide 20 only contacts the labial side of the bone 4 in such a way that none of the anatomical guide 20 is on the lingual or interior side of the patient's bone. This is important in that there is no need when using the system of this invention for any flapping any of the interior gum surface of the patient. Only a small external flap on the labial side is needed with regard to utilizing this system 100.

Figure 21:
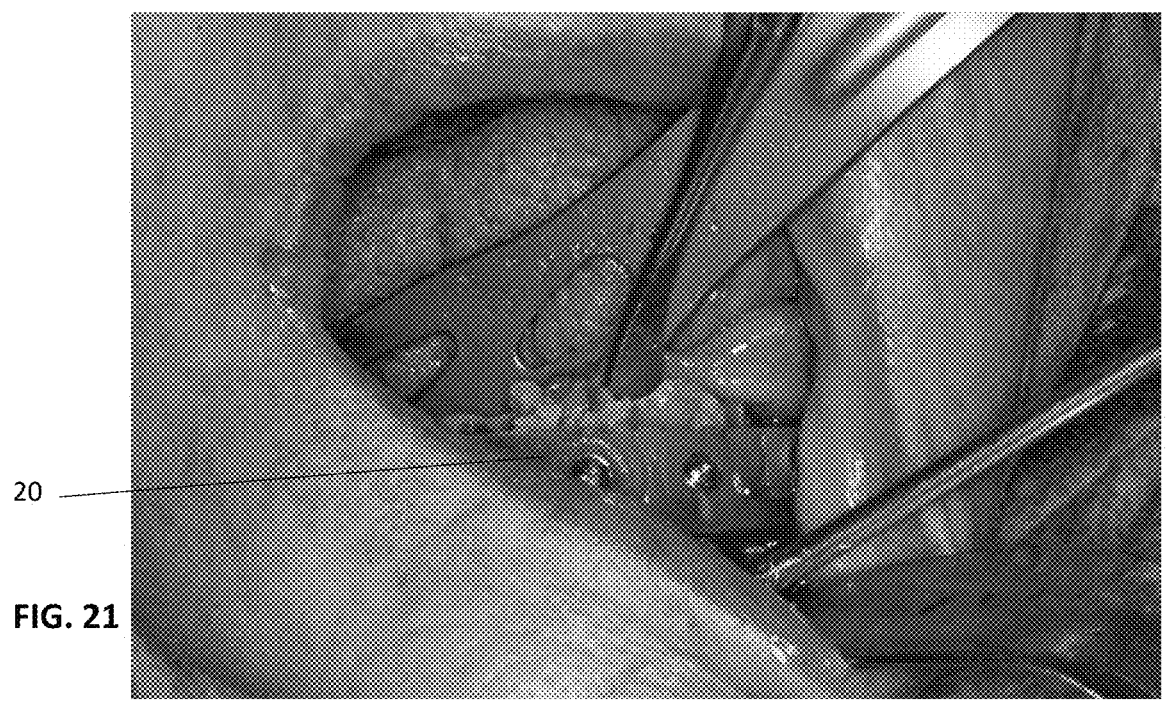
FIG. 21 shows the surgeon extracting the patient's teeth with the anatomical guide fastened to the exposed bone along the interior wall.
Figure 22:
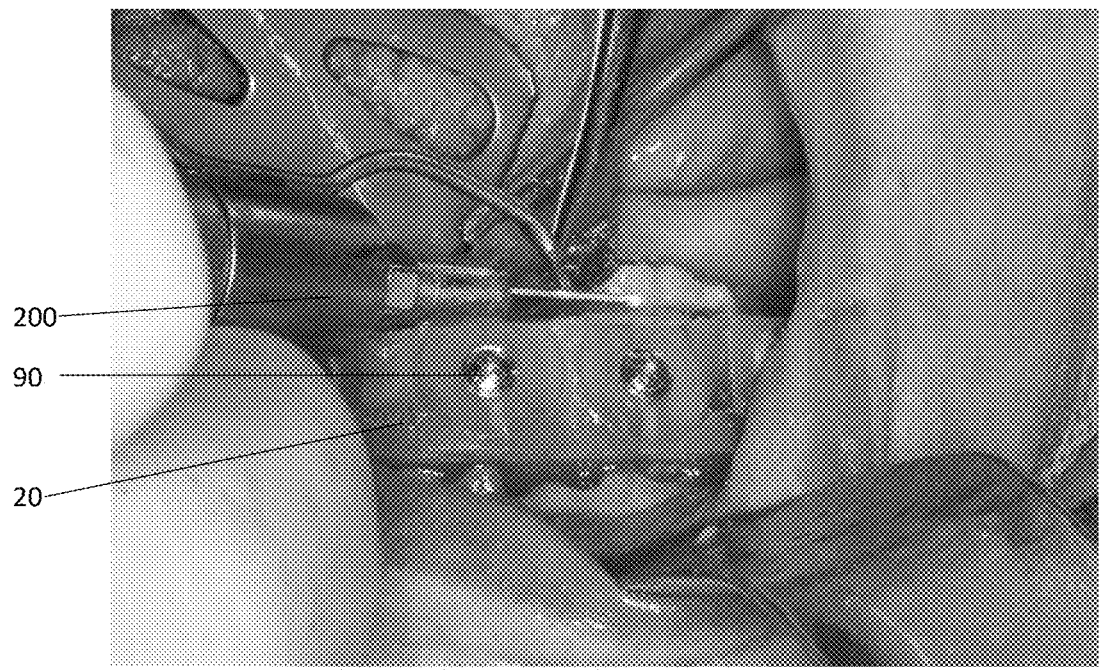
FIG. 22 is a view of the surgeon reducing the bone using the top surface of the anatomical guide to guide a reciprocating saw to reduce the bone to the level of the anatomical guide.

Once the anatomical guide 20 is securely in place, the surgeon can remove the tooth supported guide 10, extract the existing teeth 2 and then can take a reciprocating saw 200 and reduce the bone 4 such that it is flush with the anatomical guide 20, as shown in FIGS. 21 and 22. The surgeon will utilize the top surface 22 of the anatomical guide 20 to assist in establishing the distance and the amount of bone material to be removed from the patient.

Figure 5:
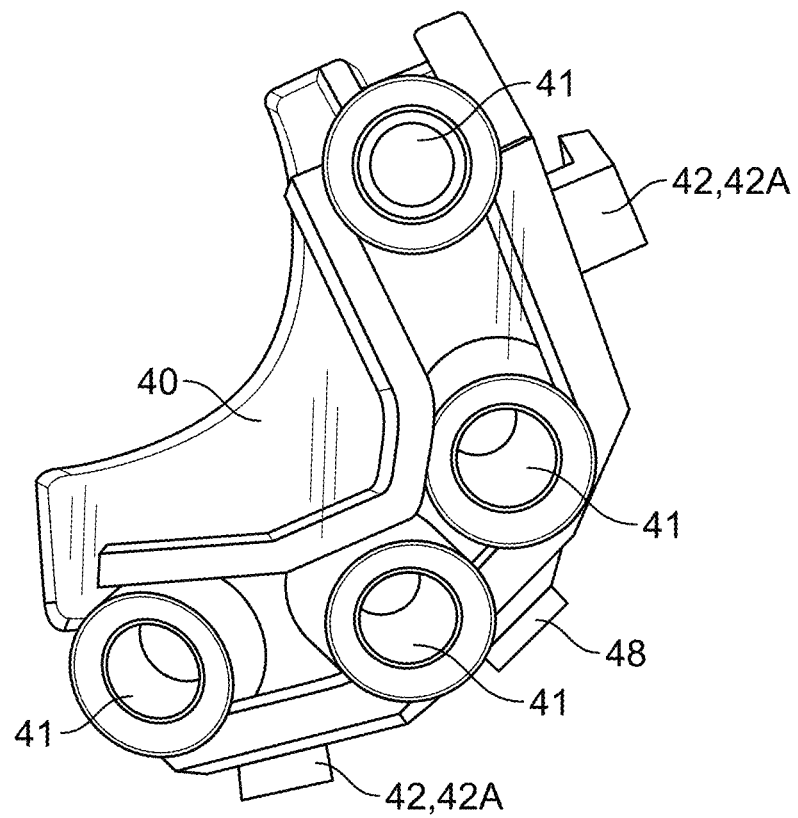
FIG. 5 is a perspective view of the surgical guide.
Figure 6:
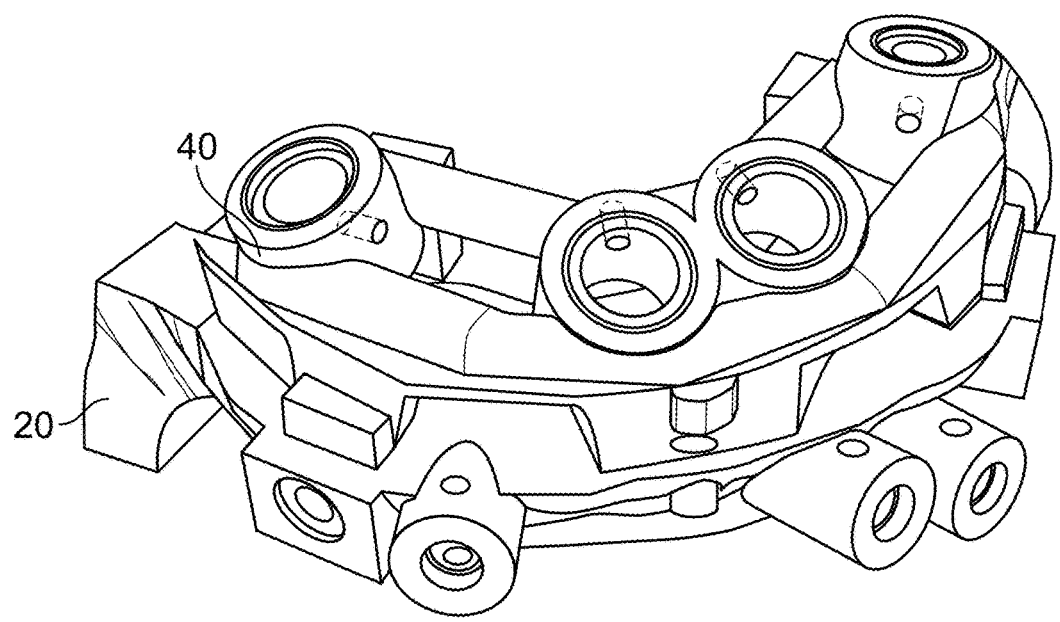
FIG. 6 is a frontal perspective view of the surgical guide shown attached to the anatomical guide for an assembly.

After the bone 4 is reduced, a surgical guide 40 can be provided, as shown in FIG. 5, that will mount directly into the connection aperture of the latch supported by the pin 92 and cantilevered over the anatomical guide 20 which has been fixed to the patient's bone 4. The surgical guide 40 has a plurality of openings 41 called drill guide openings that assist the surgeon in establishing locations to which the bone 4 will be drilled to receive implants 95. In the present invention, multiunit abutments 94 shown in FIGS. 1B and 1C1-1C3 will be used to facilitate preparing the patient's bone for receiving a prosthetic artificial tooth assembly 60. The surgical guide 40 has a plurality of support bars 42 identical to those of the tooth mounted guide 10. There is a first support bar 42 at a first end and a second support bar 42 at a second end has the similar polygonal cross-sectional shape with holes 42A to secure the surgical guide 40 exactly in place on top of the reduced bone 4 and the anatomical guide 20. There is a middle support bar 48 that fits into the middle aperture 28 of the anatomical guide 20. Once assembled, the surgical guide 40 and anatomical guide 20 form an assembly supported by pin and latch and cantilevered over implant sites, shown in FIG. 6, that is precisely and securely fastened to the bone 4. Again, as an assembly, all of the connections are provided by latches and pins in the anatomical guide 20. The surgical guide 40 has a plurality of drill guide holes 41 that enable the surgeon to precisely locate the placement of multiunit abutments 94 for later securing artificial teeth 60. As previously discussed, the surgical guide 40 can have one or at least one connection, but is shown with a plurality.

Figure 7:
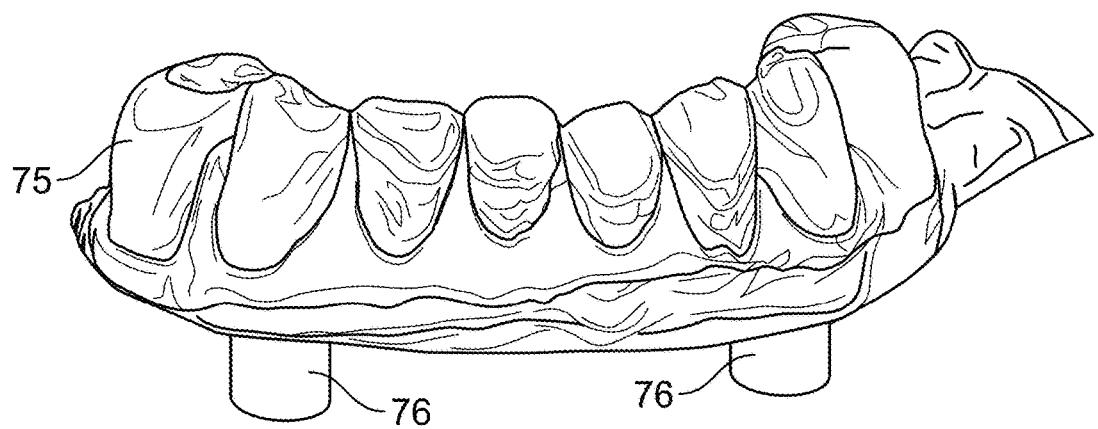
FIG. 7 is a frontal view of an articulation piece, the articulation piece is a 3D model of the patient's existing teeth and bone that was removed having a pair of pegs configured to fit into the analog model.
Figure 8:
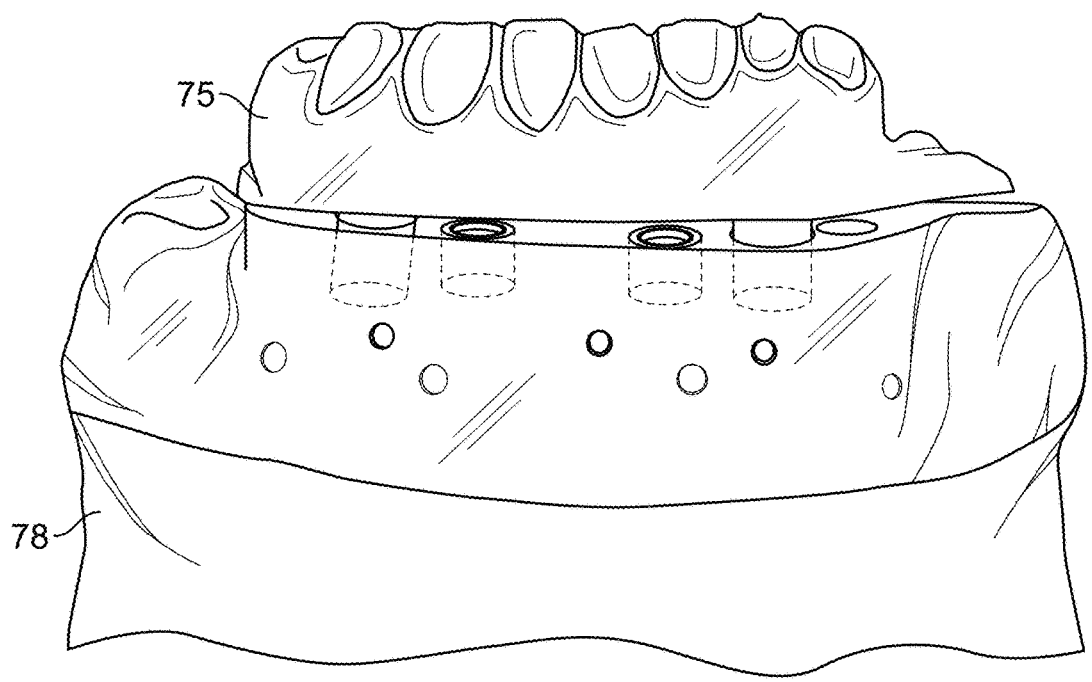

With reference to FIG. 7, the dental alignment system further has an articulation piece 75. The articulation piece 75 has a pair of pegs 76 that fit directly into openings 79 in an analog model 78. As shown the articulation piece 75 has the patient's existing teeth 2 and the bone 4 that was removed during the bone reduction process replicated. The articulation piece 75 is used to ensure for the surgeon that the bone after being reduced is properly prepared so that the alignment of the jaws is such that the existing teeth 2 can be replicated, even though they have been removed and the bone 4 has been reduced. This is shown in FIG. 8 inserted into the analog model 78, mimicking what would happen in a patient.

Figure 9:
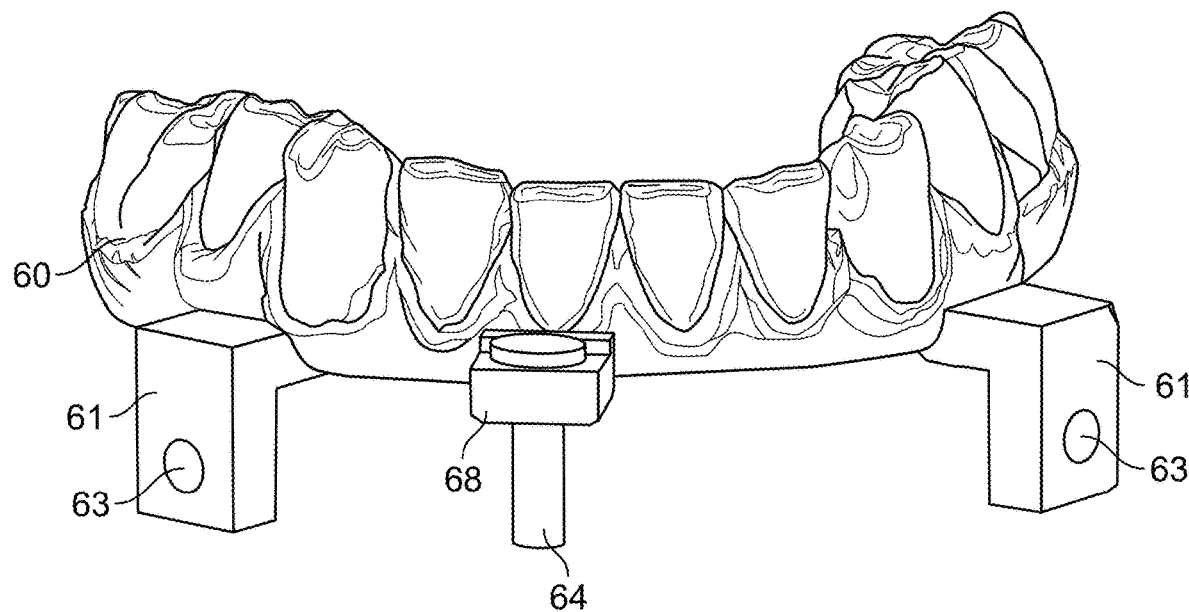
FIG. 9 is a view of artificial PMMA teeth with support bars for attachment to the anatomical guide.
Figure 10:
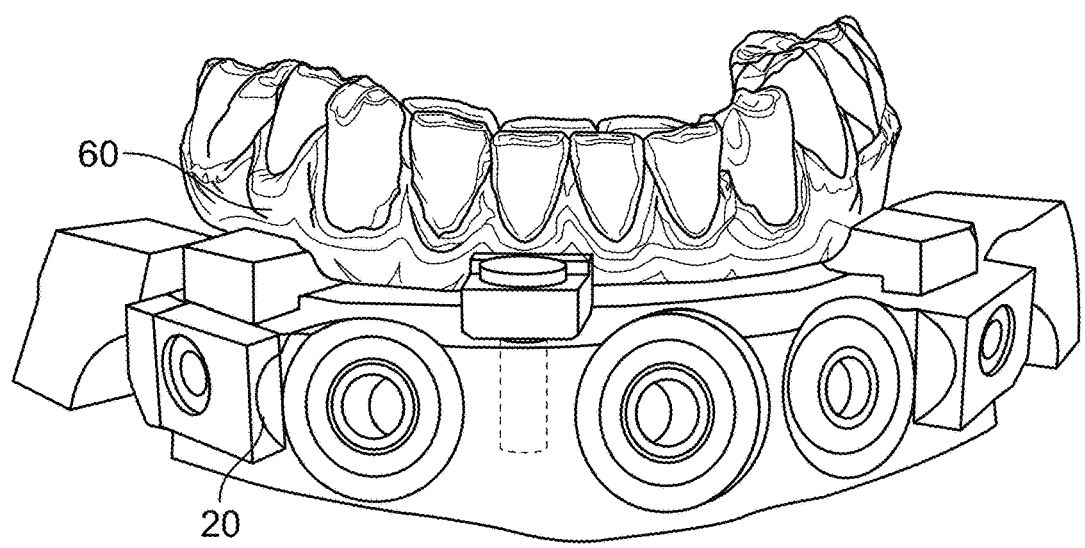
FIG. 10 is a frontal view of the artificial teeth seated on the anatomical guide.

With reference to FIG. 9, prosthetic artificial teeth 60 are shown that will be replacing the existing teeth 2. As shown, the artificial teeth 60 have a plurality of support bars 61, 68, again the support bars 61 at a first end and a second end have a cross sectional polygonal shape to fit into and be pinned to the anatomical guide 20 and a middle round peg 34. The artificial teeth support bars 61, 68 do not have an additional projection or stop like the tooth mounted guide 10, but fit directly into the apertures 24 of the anatomical guide 20 as shown in FIG. 10. As noted, the connection 11, 43, 61 into the connection aperture 24 of the anatomical guide 20 could be as few as one, but is shown with a plurality.

Figure 11:
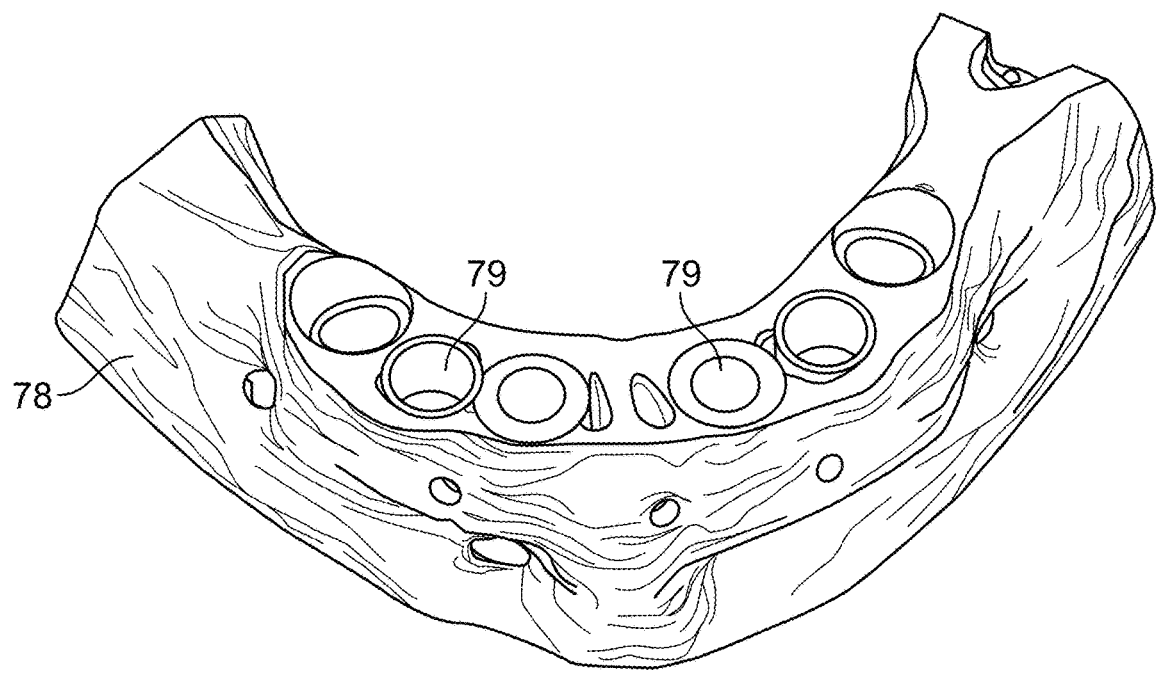
FIG. 11 is an analog model of the present invention.
Figure 12:
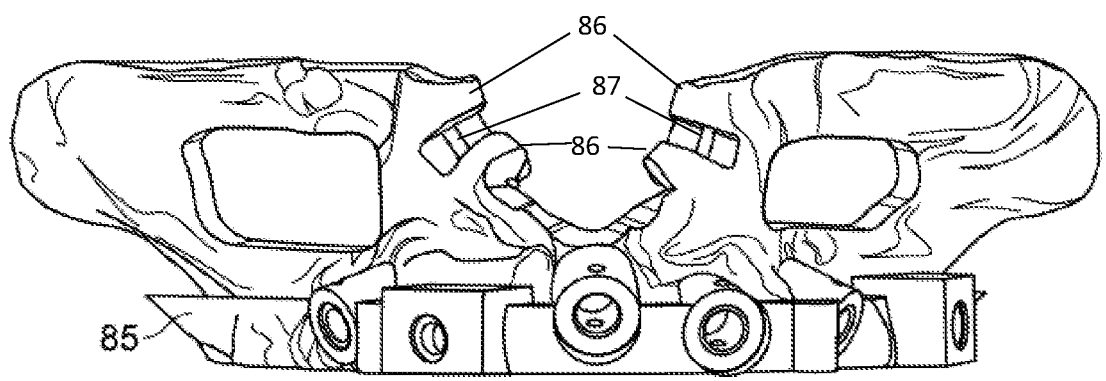
FIG. 12 is a nasal vertical mount guide of the present invention.

With reference to FIG. 11, an analog model 78 is provided showing the reduced bone and all the holes 79 used for attachment and positioning of the artificial teeth 60. The analog model 78 exactly replicates the patient's existing bone 4 and the reduction that has occurred. Holes represent where implants will be for abutment placement and titanium cylinder placement and prosthetic teeth.

In the first embodiment illustrated, the system 100 was shown being used on the mandible or lower teeth. The dental alignment system 100 is equally suited to be used on the upper teeth using the anatomical guide 20 with or without a tooth supported guide 10 or optionally using the anatomical guide 20 with a nasal vertical mount 85 in such a fashion that support is provided by the nasal bone structure. The nasal vertical mount 85 has a similar "U" shaped cross section and can be fitted on the front facial bone and nasal floor. In this embodiment, the anatomical guide 20 has a nasal vertical mount portion 85 integrally formed or otherwise affixed to an opposing outer surface relative to the flat outer surface. The nasal vertical mount portion 85 extends from the anatomical guide 20 to buttress against cheek bones. The portion has nasal clips 86 configured to assist in vertically positioning the anatomical guide interior surface against the exposed bone of the maxilla. In the preferred embodiment, each nasal clip 86 has an aperture 87. The combination of the tooth supported mount 10 with the anatomical guide 20, or the anatomical 20 with or without the nasal vertical mount 85 allows the surgeon to accurately do both arches, in other words he can do a procedure on the lower teeth and sequentially can do the upper teeth while the patient is under sedation. This is made possible in part due the rapid and precise nature that allows the surgeon to operate quickly with sufficient amount of time to achieve both procedures at one time if so desired. Additionally, as noted and as will be seen, during the procedure, the surgeon can irrigate and flush and drain blood and other tissue during the procedure due to the windows in the different components and spacing between the components that allow the surgeon to visually see the drill holes as he proceeds. This will be described later in the discussion of the device. To summarize, for the lower arch, a surgeon can seat the anatomical guide 20 on facial bone only or use the tooth supported guide 10 and the anatomical guide 20 combined. There are three options of support for the upper arch, the first two are identical to the lower arch, one; tooth and facial anatomy, two; facial anatomy; or the third, specific to the upper arch, facial anatomy and nasal bone structure. In all cases, the anatomical guide 20 is used. Due to the accuracy of the interior wall 21 of the anatomical guide 20, to match the labial bone, providing an intimate matching fit to this facial bone, a skilled or experienced surgeon can use the anatomical guide 20 only, proceeding and securing the anatomical guide 20 to this bone. this feature and capability make the anatomical guide 20 unique compared to all other prior art guides. The Surgical Guide 40 is rigidly supported by the latches or connections on the support bars 42, 48 at the connection apertures 24 of the anatomical guide 20. There is a space between the Surgical Guide 40 and the Anatomical Guide 20. This creates a gap preventing the surgical guide 40 from sitting on the top surface and cutting surface 22 of the anatomical guide 20. This gap keeps damage from the doctor cutting the anatomical guide 20 accidentally from preventing the seating of the surgical guide 40. The Surgical Guide 40 is cantilevered over the Anatomical guide 20 and the bone. The tooth supported guide 10 will also rest on the latches or connections on the support bars 11, 18 at the connection apertures 24 and cantilever over the anatomical guide 20. Similarly, the prosthetic teeth 60 are held in a planned position over the abutments 94. As used herein, the latches or connections are referred to as "Diamond Latches" by the inventor. These latches form the connections of the various parts to the anatomical guide 20. These connections represent each of support bars 11, 18, 42, 48, 61, 68 of the various devices to be attached to the anatomical guide 20 that fits at an end into the connection apertures 24 of the anatomical guide 20. The end has a hole that is pinned to the anatomical guide 20 at each support bar 11, 42, 61. All the support bars have an enlarged section that abuts against a top surface at the connection aperture 24 to form the rigid connections.

A rough schematic is provided in FIG. 13 indicating the general implant procedure. In this procedure, it must be understood that the components that have been pre-fabricated using a 3D scanned laser image to mimic surfaces of the various components needed to fit precisely in the patient's mouth. When all the components have been made, the patient can be taken into the operating room. The first step will be to create a flap buccal or labial of the patient. In this case the flap is a portion of the soft gum tissue that is removed from the bone 4 and folded back so the anatomical guide 20 will fit tightly against the bone 4. The second step is the seating of the anatomical guide 20 with or without using the tooth mounted guide 10 or vertical mount that will sit on the teeth 2 and bone 4 anatomy of the patient. In the next step, the anatomical guide 20 will be screwed or fastened to the patient. The fourth step requires the vertical mount 10 to be removed. The fifth step requires the teeth 2 to be extracted and the bone reduced or reduce bone with the teeth in place. The sixth step requires the surgical guide 40 to be connected to the anatomical guide 20. The seventh step requires the implants 95 to be placed, the implants 95 as will be seen later are multiunit anchors that provide anchoring locations for the artificial teeth 60. The anchoring locations are optionally multiunit abutments 94. Step 8 is the optional abutments 94 placed and titanium cylinders. Step nine is the artificial teeth with latches are connected to the anatomical guide and in step ten, titanium cylinders 98 are looted in the artificial teeth 60, the cylinders 98 are fixed to the artificial teeth 60. The artificial teeth 60 can then have the connection or support bars removed and be prepared for implantation.

Prior to a patient going into surgery, a complete 3-dimensional digital image, CT scan or laser scanning of the patient's mouth with the existing teeth in place is made. The CT scan and the digital images of the teeth are imported into a software to plan implant placement. This plan will be used to create the reduction, implant guide, analog model and all other pieces. From this scan, the various guides are made, including a complete fabrication of the artificial teeth that will be replacing the patient's failing teeth.

The various components of the dental alignment guide system 100 including those replicating the patient's existing teeth called the articulation piece 75 and the analog model 78 as well as all the other guides can be made using a pre-fabricated 3-D printing that precisely and accurately matches the patient so a proper fit of the artificial teeth 60 can be achieved with a minimal amount of time.

Figure 14:
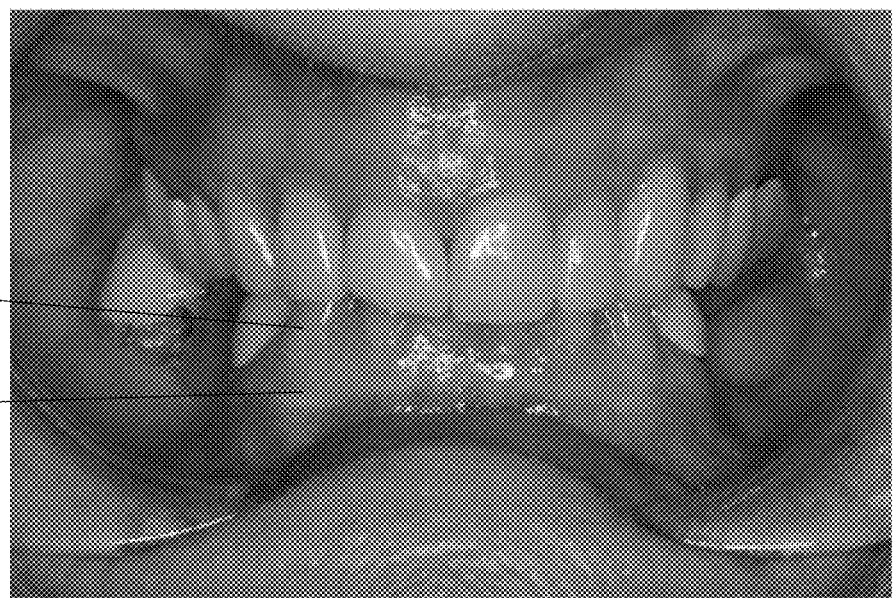
FIG. 14 is a frontal view of a patient being prepared for dental surgery showing the teeth and gums prior to flapping.
Figure 15:
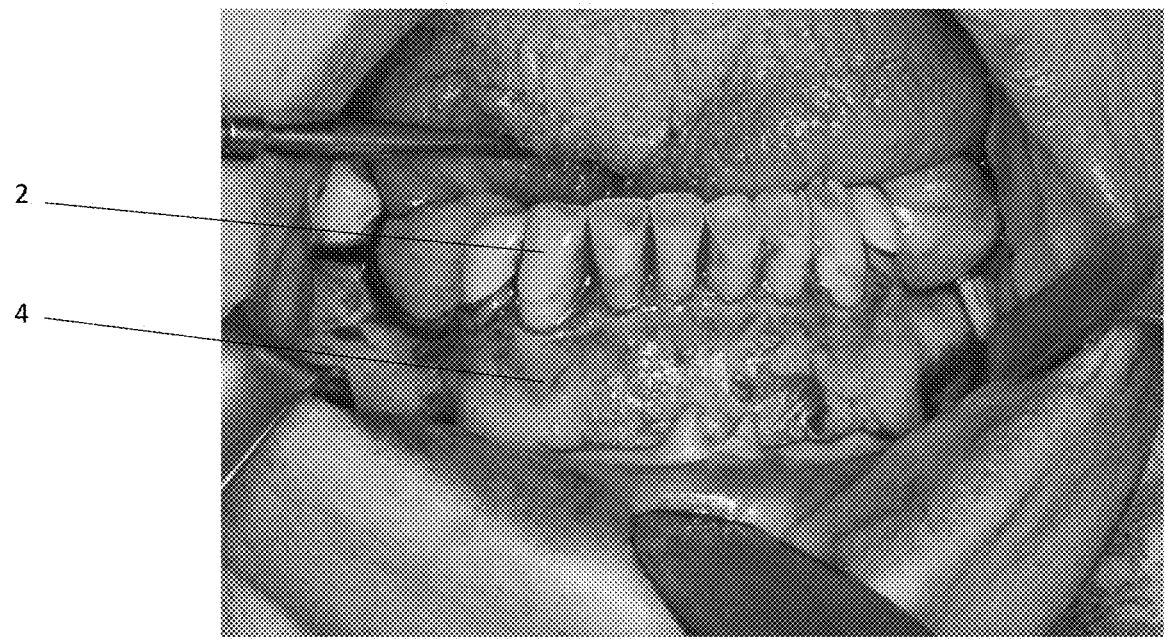
FIG. 15 is the frontal view of the patient of FIG. 14 showing the teeth and exposed bone after the gum tissue has been flapped.

With reference to FIGS. 14-39, an exemplary procedure is shown wherein the dental alignment system 100 and its associated components are employed. As shown in FIG. 14, the patient's front teeth 2 with the soft gum tissue 5 still intact is shown. In FIG. 15, the same front teeth 2 with the soft tissue 5 flapped is illustrated. As shown, the soft tissue 5 is only removed on the labial side of the patient's front teeth 2, between the lips and the mandible.

Figure 16:
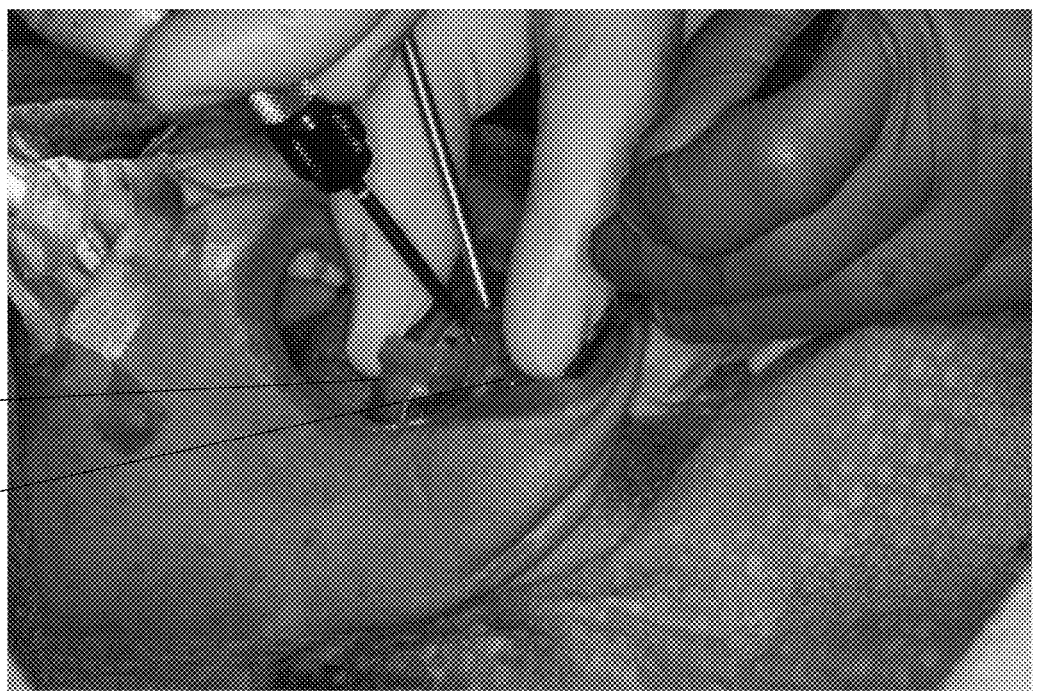
FIG. 16 is a view of the patient showing the surgeon placing a tooth supported guide and anatomical guide onto the patient's teeth and exposed bone.
Figure 17:
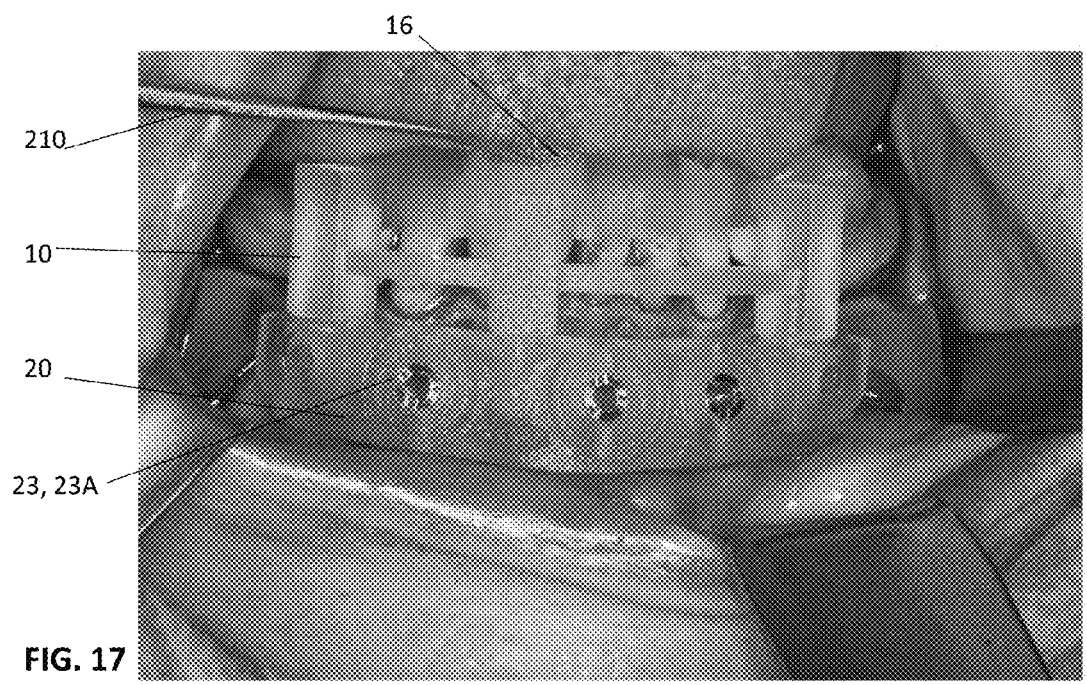
FIG. 17 is a frontal view of the tooth mounted guide and the anatomical guide assembly showing a tool being placed through a window opening to verify the tooth supported guide is properly resting on top of the teeth.

With reference to FIG. 16, the anatomical guide 20 and the teeth mounted guide 10 are shown as an assembly placed over the patient's existing teeth 2. As illustrated, the tooth supported guide 10 rests on top of the teeth 2 as evidenced by the probe 210 that is passed through the window 16 to verify that the tooth supported guide 10 is positioned fully resting on the top of the teeth 2. At this point in time, the anatomical guide 20 is shown not affixed to the bone, however, it is attached securely but not yet pinned to the three support bars 11, 18 as shown in FIG. 17. The support bars 11 in proximity to the first end and second end have a polygonal shape as shown, shaped rectangular or square and fits into a connection aperture 24 on the anatomical guide 20.

Figure 18:
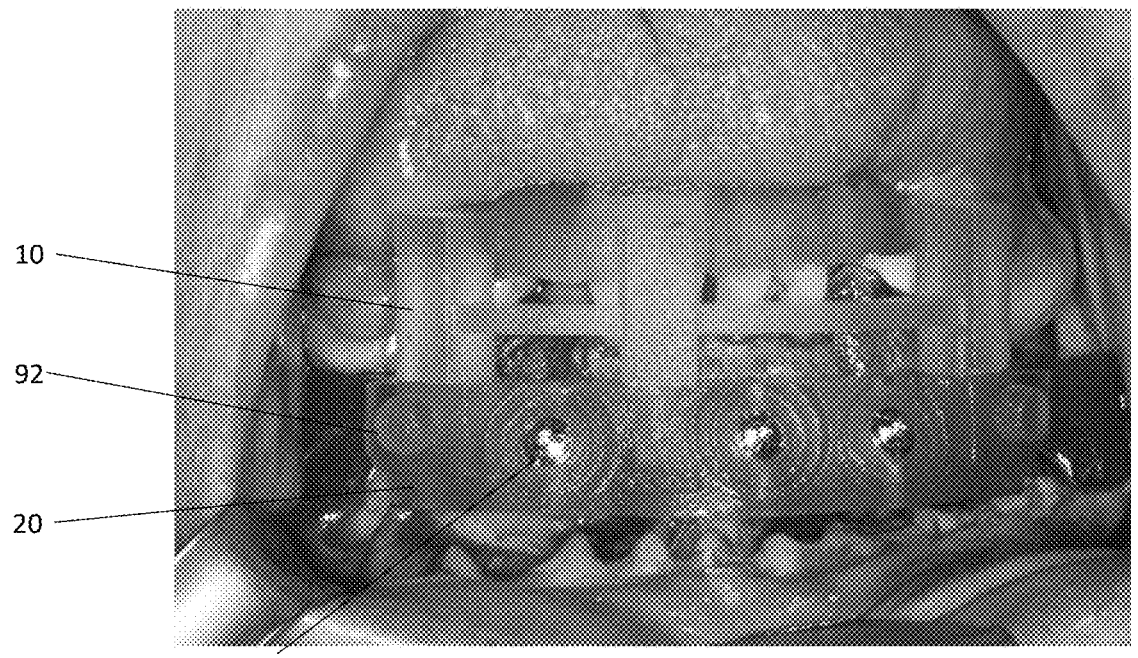
FIG. 18 shows the assembly fitted onto the teeth after the surgeon has removed two teeth that would have interfered with screw placement, as shown three screws are illustrated fastening the anatomical guide to the labial side of the exposed bone and two alignment pins are also shown securing the tooth supported guide to the anatomical guide.
Figure 19:
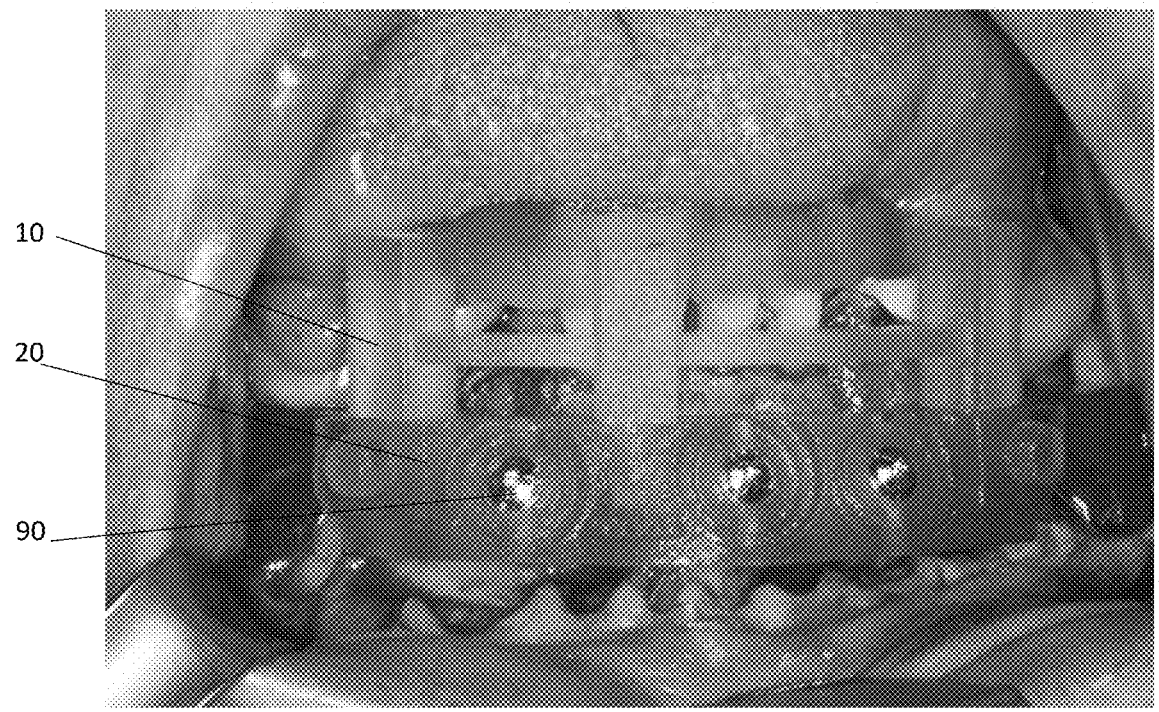
FIG. 19 is an enlarged view of FIG. 18.
Figure 20:
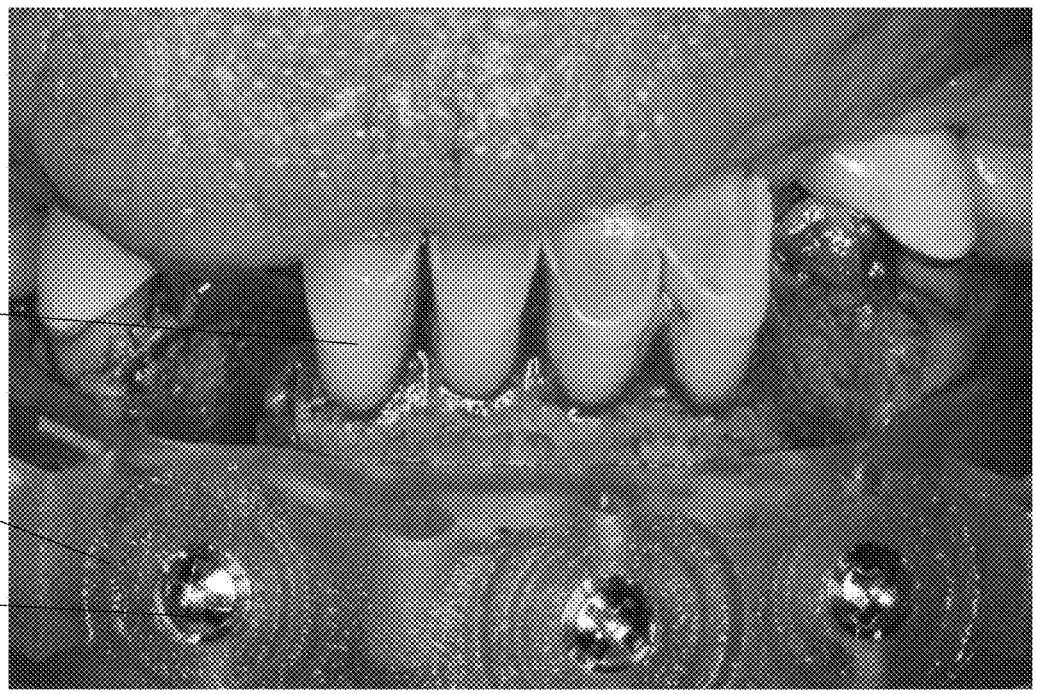
FIG. 20 is a view of the anatomical guide securely fastened to the patient's bone with the tooth mounted guide removed.

Holes 13 provided in the tooth supported guide 10 at the ends of the support bars 11 in proximity to the ends of the anatomical guide 20 align with holes 24A in the connection apertures 24. The holes 24A in the connection apertures 24 and the holes 13 in the tooth supported guide 10 are aligned and can be pinned together to complete the assembly. Pins 92 are not shown in this view of FIG. 17, but are shown in FIGS. 18 and 19. These pins 92 lock and support via a latched assembly of the two parts. As shown in FIGS. 18 and 19, the anatomical guide 20 has a plurality, as shown 3 fastener holes 23, for connection to the bone 4 of the patient. These fastener holes 23 can optionally have a metal sleeve 23A or bushing, best shown in FIG. 17, to provide additional support and strength to the anatomical guide 20 when the fasteners 90 are inserted as shown in FIG. 20.

With reference to the FIG. 17, when the bone guide 20 and tooth mounted guide 10 assembly are positioned in the patient's mouth, it may be possible that the screw hole openings will align directly into a tooth 2 or a root of a tooth and as a result, the surgeon may desire to extract those teeth that interfere with the attachment of the bone screw 90. As shown in FIGS. 18 and 19, two teeth have been removed in this example to allow the screws 90 to be attached without permanently leaving remnants of the roots of the tooth. As shown, pins 92 are placed in the alignment holes 24A at this point in time. These pins 92 secure the tooth supported guide 10 directly to the anatomical guide 20. Screws are then placed into the openings and the anatomical guide 20 is drawn tightly and firmly against the exposed bone 4. This is as shown in FIGS. 16, 17, 18, and 19.

Figure 23:
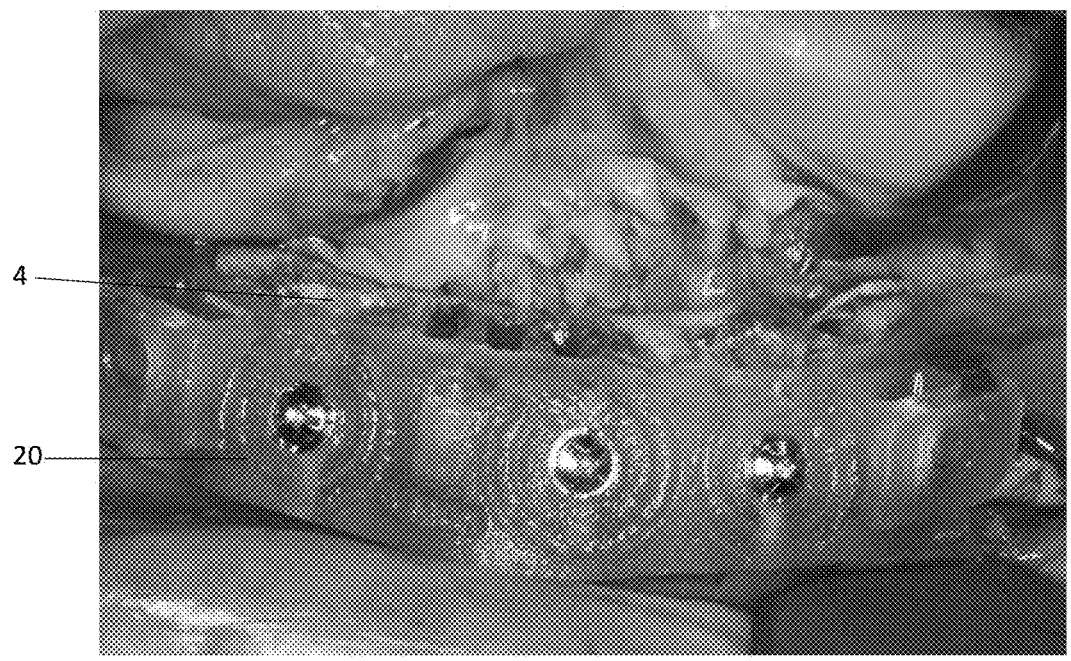
FIG. 23 is a view showing the bone after being reduced from a generally frontal perspective.
Figure 24:
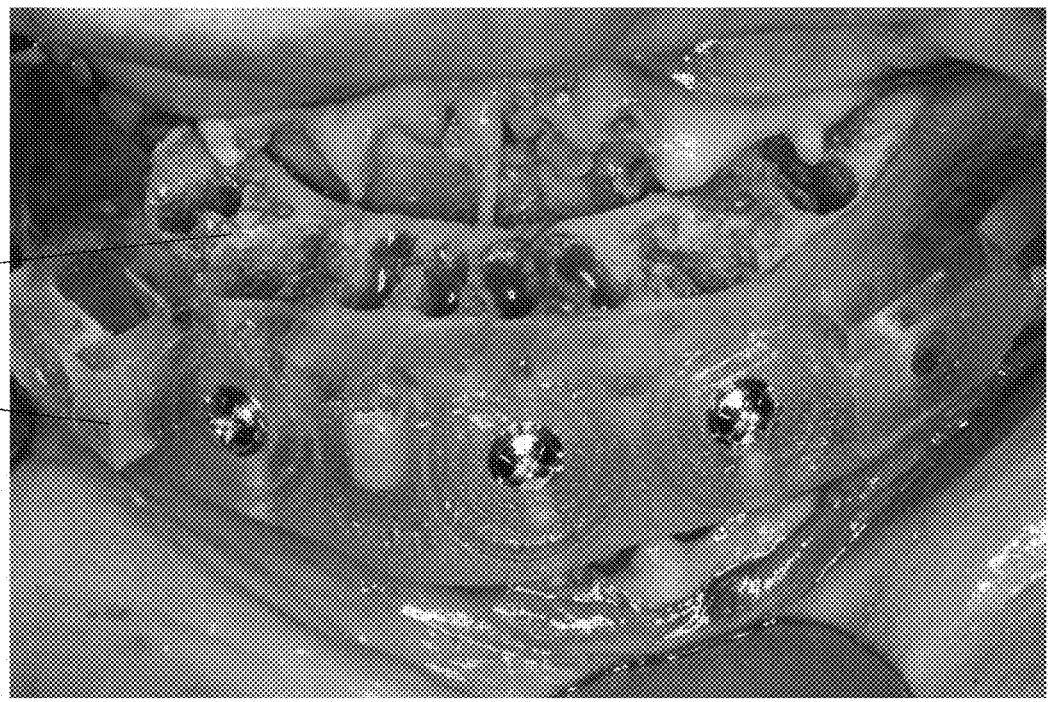
FIG. 24 is a view showing the bone after being reduced from a generally top perspective.

Once the anatomical guide 20 is firmly attached to and fastened to the bone 4, the tooth supported guide 10 can be removed from the assembly. As illustrated in FIG. 20, once the tooth supported guide 10 is removed, the teeth are extracted and the bone is reduced, or optionally the bone can be removed with the teeth. The surgeon can then reduce the bone 4 down to the level of the bone guide surface 22 using a cutting tool optionally a reciprocating saw 200. The outer top surface 22 of the anatomical guide 20 is used to help guide the reciprocating saw 200 to make the necessary cuts as illustrated in FIG. 22. When fully reduced, the bone 4 is flush with the surface 22 of the anatomical guide 20 as illustrated in FIGS. 23 and 24.

Figure 25:
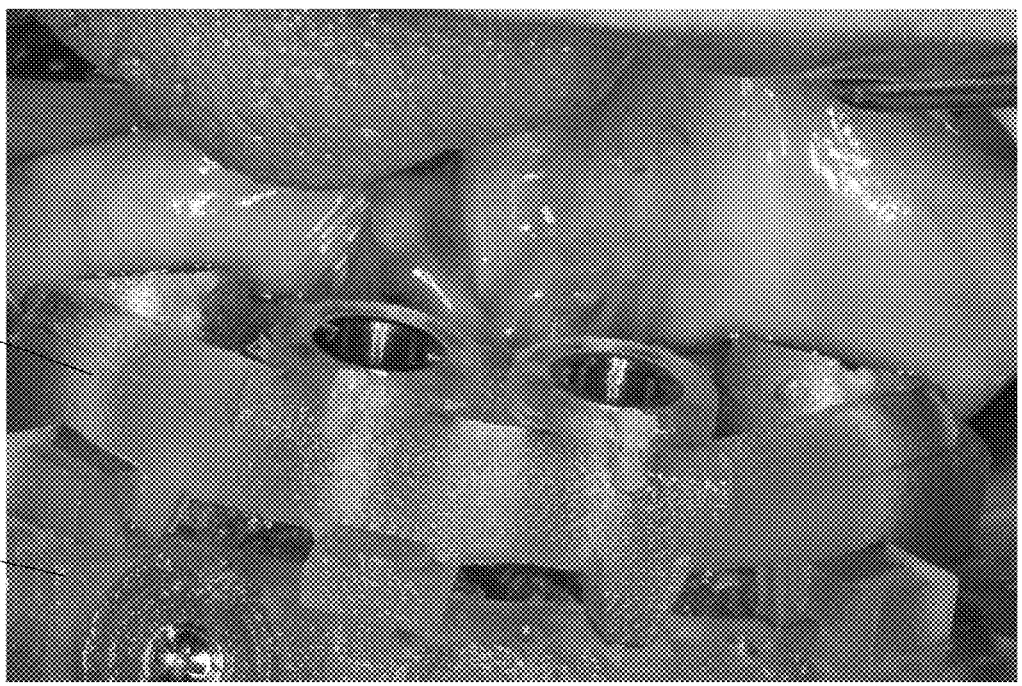
FIG. 25 is a view of a surgical guide mounted onto the anatomical guide over the reduced bone.
Figure 26:
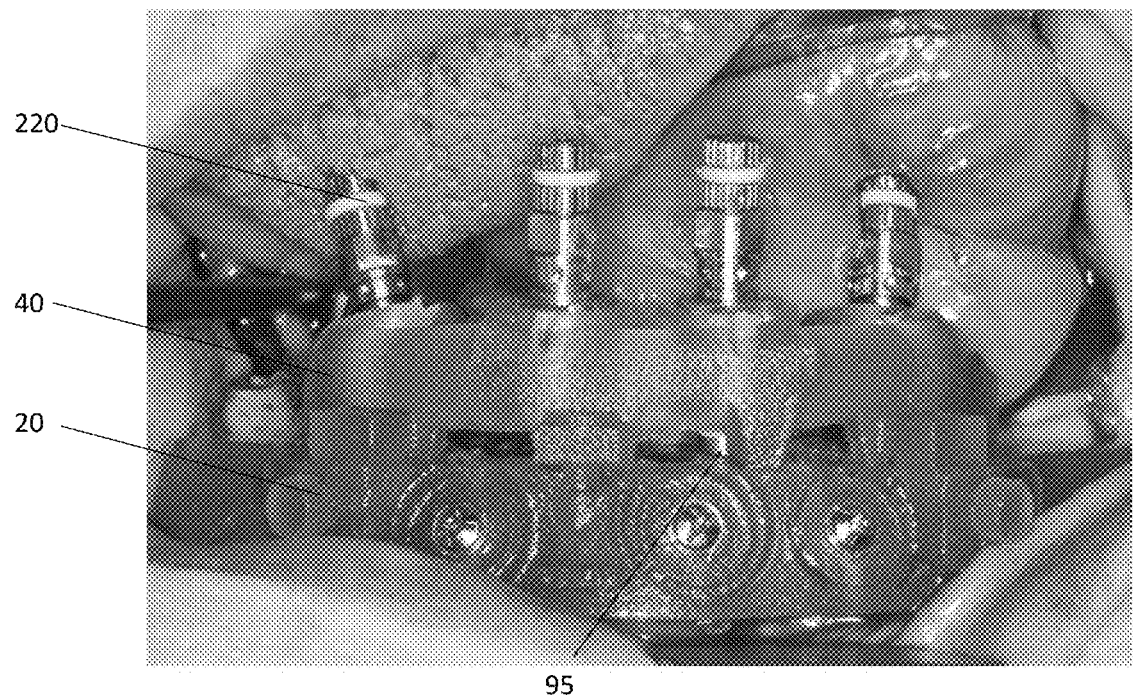
FIG. 26 is a view of implant drivers positioned into the surgical guide.
Figure 27:
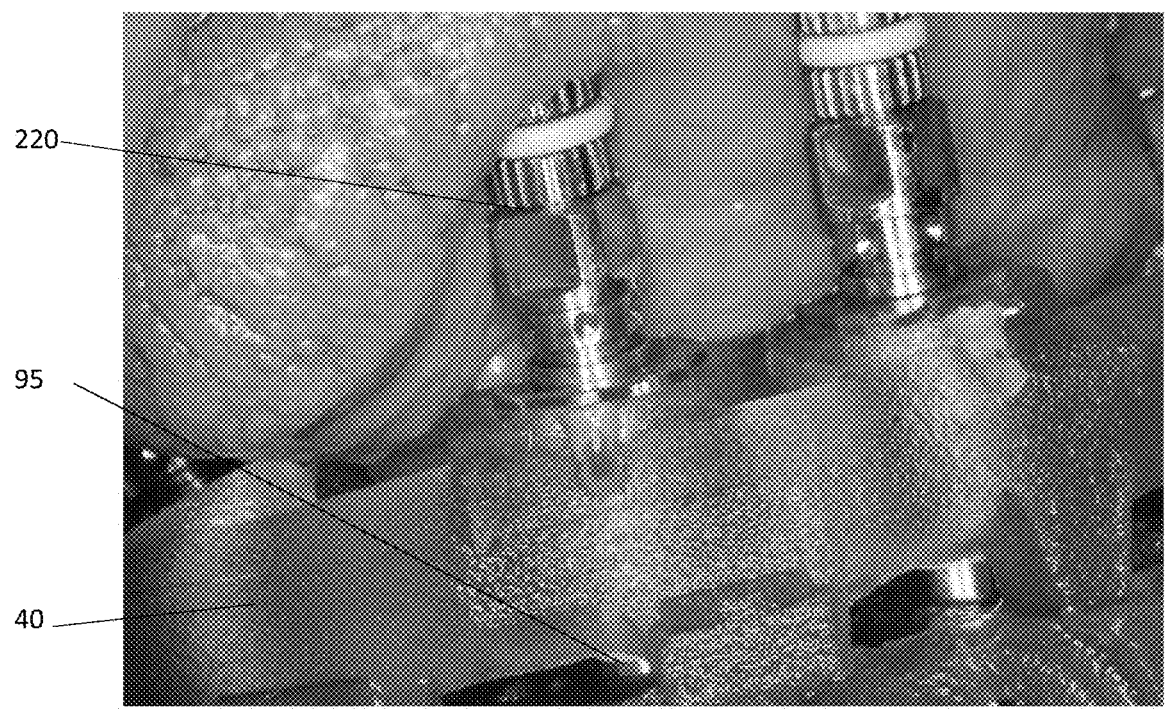
FIG. 27 is an enlarged view of two of the drivers on a left side of the surgical guide, the space between the surgical guide and the anatomical guide providing visual access for the surgeon.
Figure 28:
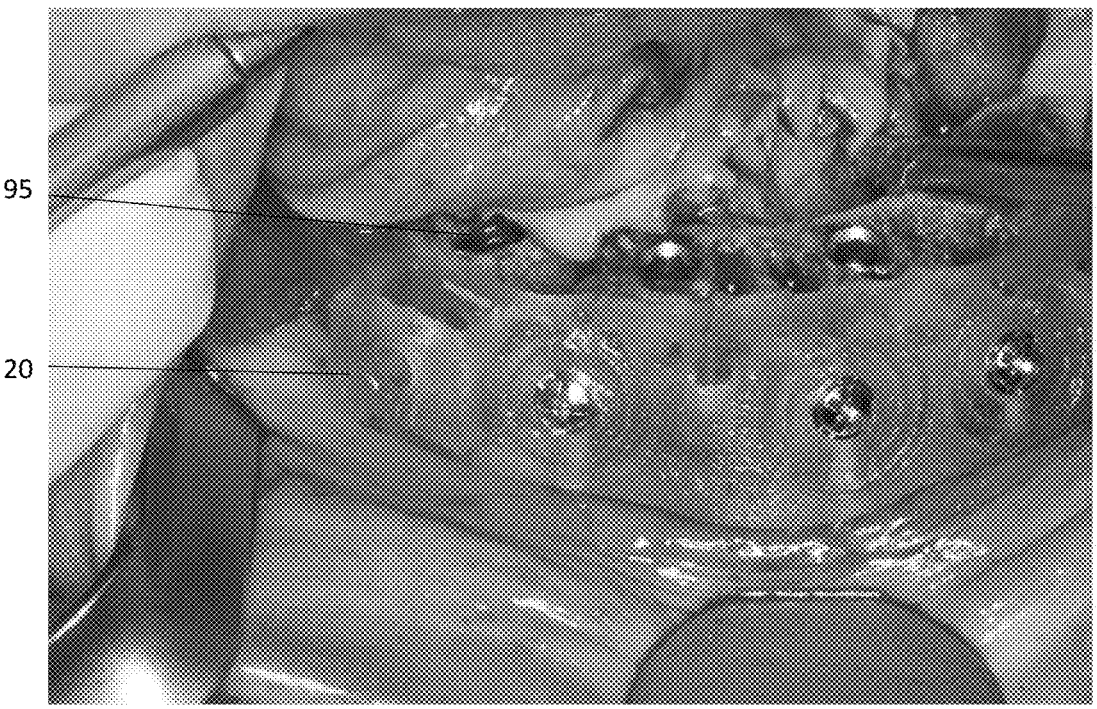
FIG. 28 is a view showing the anatomical guide with the surgical guide removed.

With reference to FIG. 25, it is now possible to place the surgical guide 40 support bars into the connection apertures of the latches and inserting pins 92 to support the surgical guide cantilevered over the anatomical guide 20. The surgical guide 40 has alignment tubes in the form of openings for placement and guiding a drill and positioning implants. As shown in FIG. 26, the implant drivers are illustrated. As shown the implant drivers 220 are driving the implant 95 into the reduced bone 4. In doing so, the implant drivers 220 while being rotated are being controlled in depth, angulation and rotation. As shown in FIG. 28, once the surgical guide 40 is removed the implants 95 are shown implanted into the reduced bone 4 at proper depth and angulation. Once the implants 95 are positioned, a prosthetic seat 80 can be placed over the implants 95 to place the abutments 94 to attach to the implants 95, as shown in FIG. 29.

Figure 30:
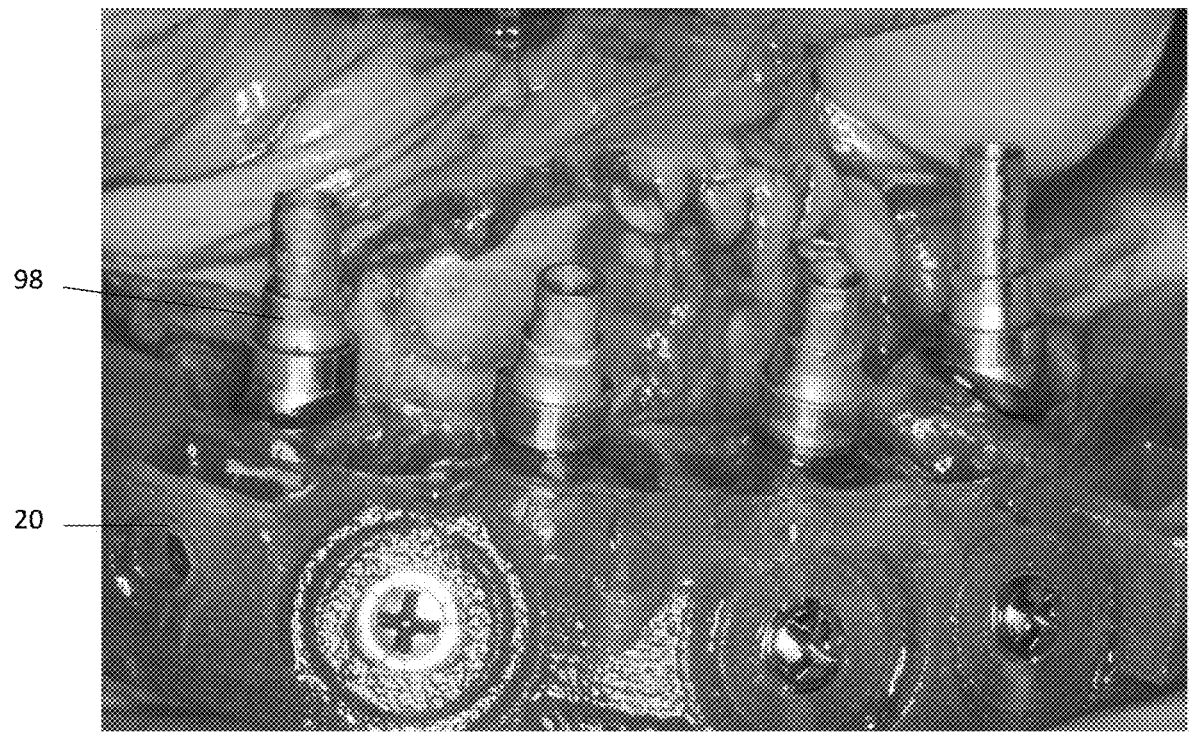
FIG. 30 is a view of pre-cut to length cylinders placed onto the abutments driven and secured to the reduced bone with the anatomical guide in place.

As shown in FIG. 30, cylinders 98 are placed on the end of the multiunit abutments 94. These cylinders 98 have been cut to a predetermined length to match the prosthetic artificial teeth 60 that will be inserted later. These temporary cylinders 98 are substantially longer than are required for the actual implant and, therefore, by knowing the precise depth and length of the artificial teeth, the cylinders can be cut precisely to a length and marked where they go into the openings of the artificial teeth 60 pre-cut. This saves a tremendous amount of time in that the cylinders 98 are now pre-cut to the proper length prior to being inserted onto the abutments 94.

Figure 29:
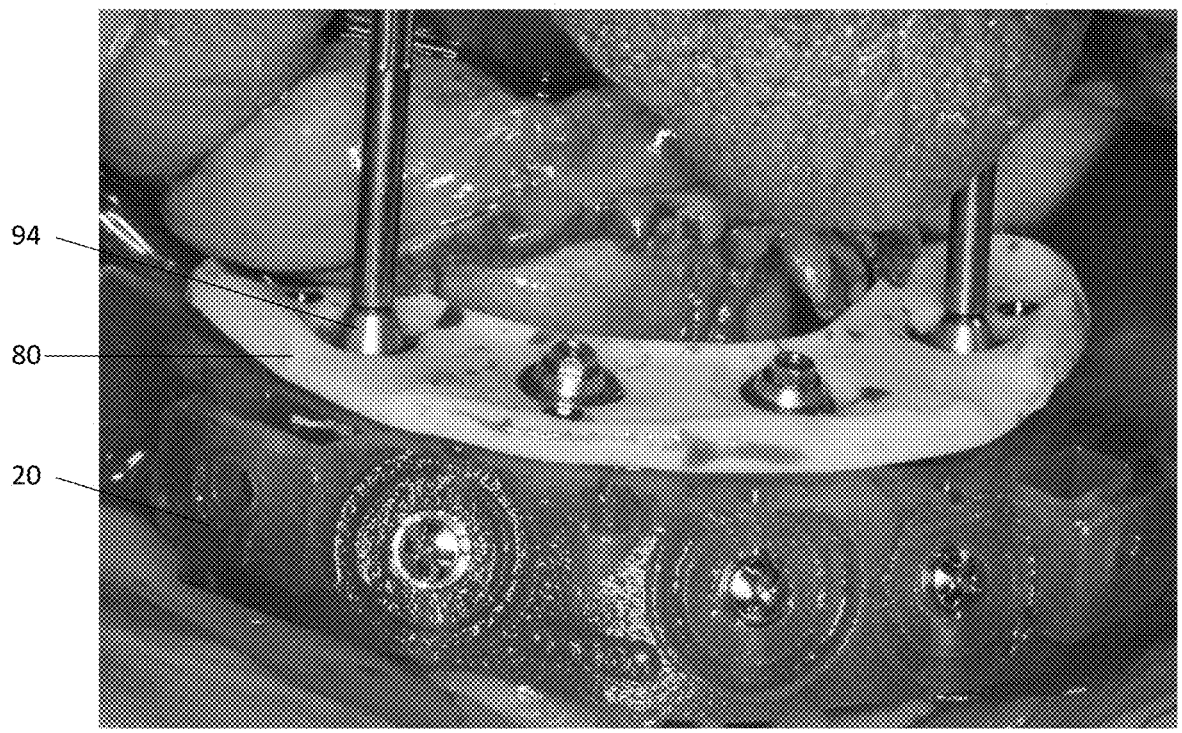
FIG. 29 is a view of a prosthetic seat positioned over the implants, the prosthetic seat is an optional device used to seat the abutments.
Figure 31:
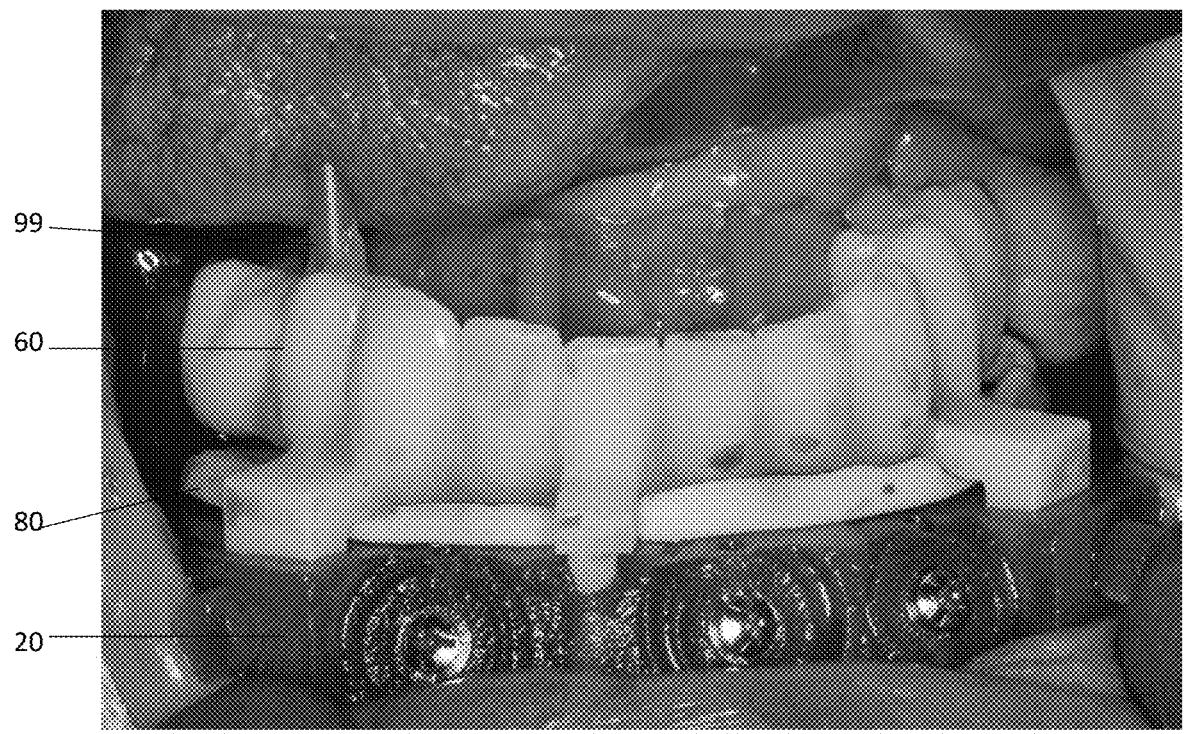
FIG. 31 is a view showing PMMA artificial teeth with support bars attached and pinned to the connection attachments of the anatomical guide with the prosthetic seat being between the reduced bone and the bottom surface of the artificial teeth, the teeth having holes configured to receive the pre-cut cylinders which have short straws placed in each cylinder opening.
Figure 32:
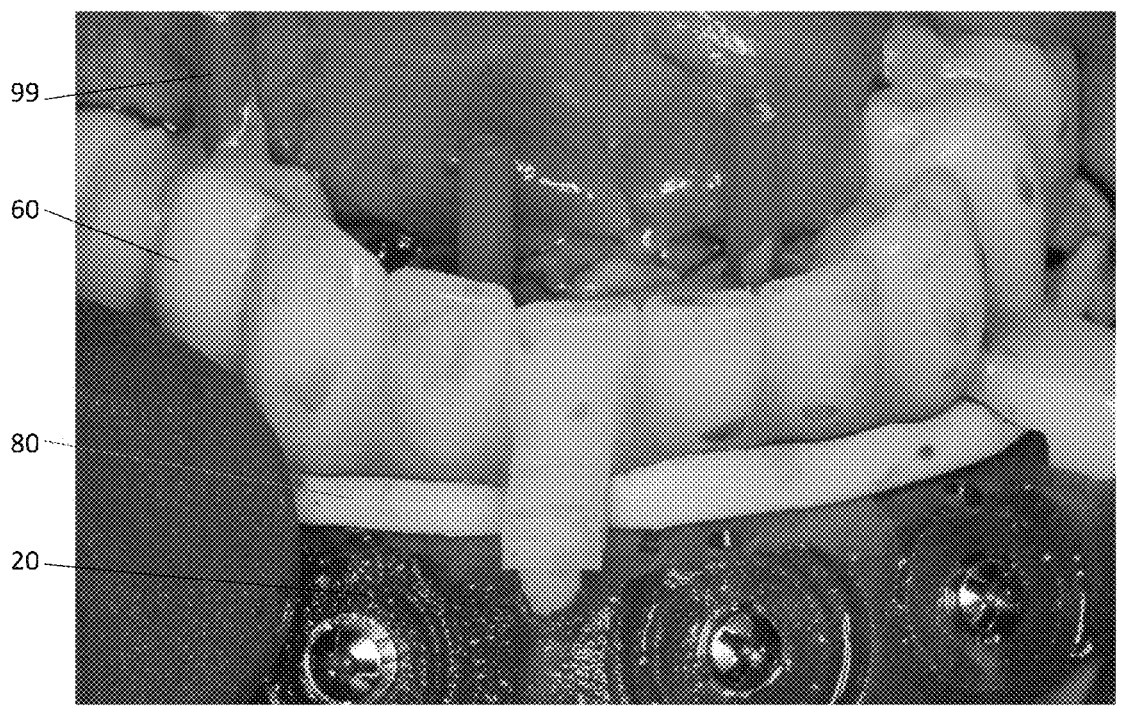
FIG. 32 is a view taken from FIG. 31 showing the cylinders being looted in place using a light curing adhesive.
Figure 33:
FIG. 33 is a top view of the artificial teeth after being removed from the anatomical guide showing the cylinders fixed in place.
Figure 34:
FIG. 34 is a bottom view of the artificial teeth showing the enlarged bottom of the cylinders configured to fit onto the implants.

As shown in FIG. 29, the prosthetic seat 80 is shown, the prosthetic seat 80 is generally an elastomeric piece that can be produced in the lab, it replicates or simulates the gum tissue that will grow back and it will sit between the reduced bone 4 and the artificial teeth 60. The prosthetic seat 80 is shown in FIGS. 31 and 32. The artificial teeth 60 are placed over the cylinders 98 into position, the artificial teeth 60 have support bars 61, 68 similar to those of the tooth supported guide 10 and the surgical guide 40. These support bars 61, 68 have ends that complimentarily fit into the anatomical guide 20 as previously discussed. As shown, pins 92 are positioned through the holes 24A in the attachment connections 24 and through artificial teeth through the support bar holes 63 at each proximal end. The middle support bar 68 is a round pin 64 that fits into the anatomical guide 20 as previously discussed. When the artificial teeth 60 are placed into position, small removable straws 99 are placed in each cylinder 98 these are put in place prior to applying a light curing adhesive around each cylinder 98. The cured adhesive 97, shown in FIG. 34, is provided to securely fasten the cylinders 98, shown in FIG. 30, directly to the artificial teeth 60. Once cured the surgeon can then remove the artificial teeth 60 and the cylinders 98 will be permanently attached to the artificial teeth 60 shown in FIG. 33 in a top view and FIG. 34 in a bottom view.

Figure 35:
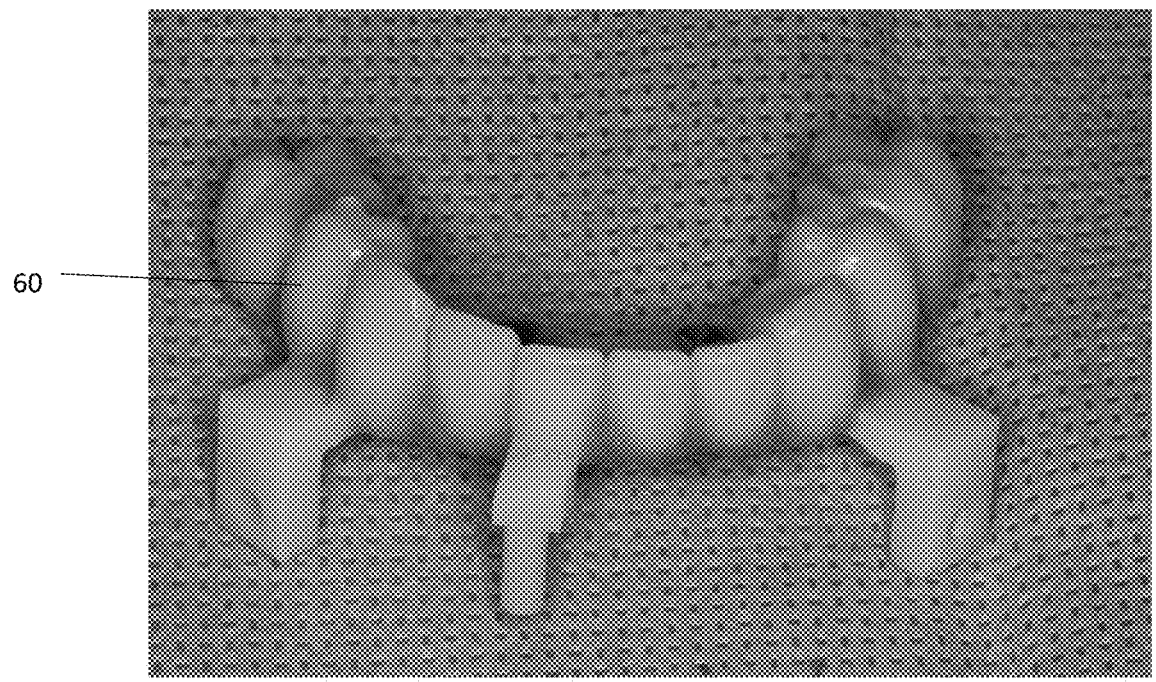
FIG. 35 is a tilted frontal view of the artificial teeth.
Figure 36:
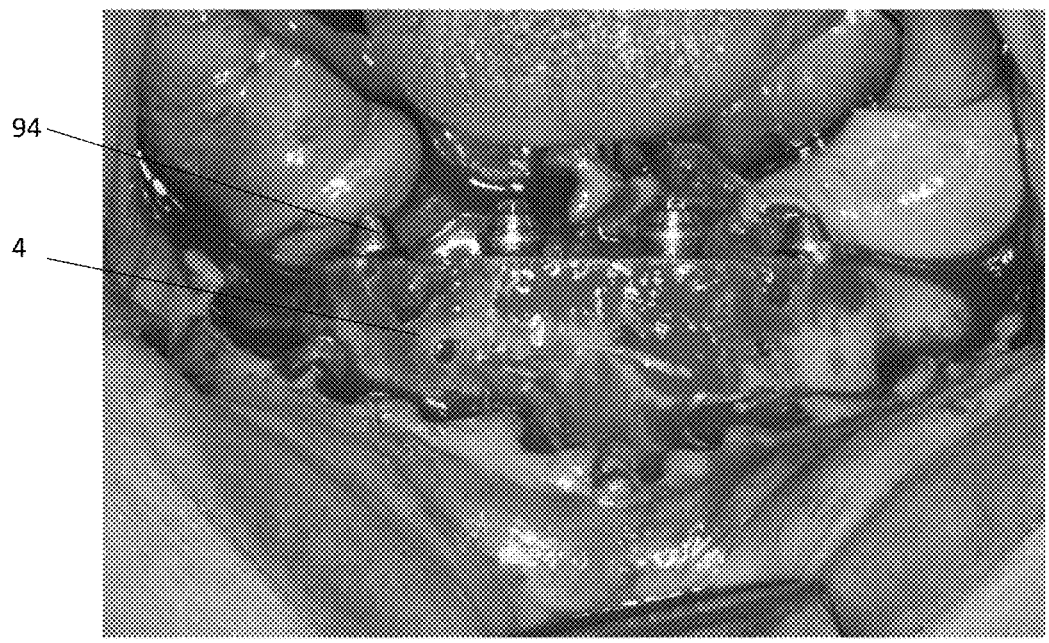
FIG. 36 is a view of the reduced bone with the abutments projecting slightly and the exposed bone with the anatomical guide removed prior to the surgeon grafting and suturing the gum flap.
Figure 37:
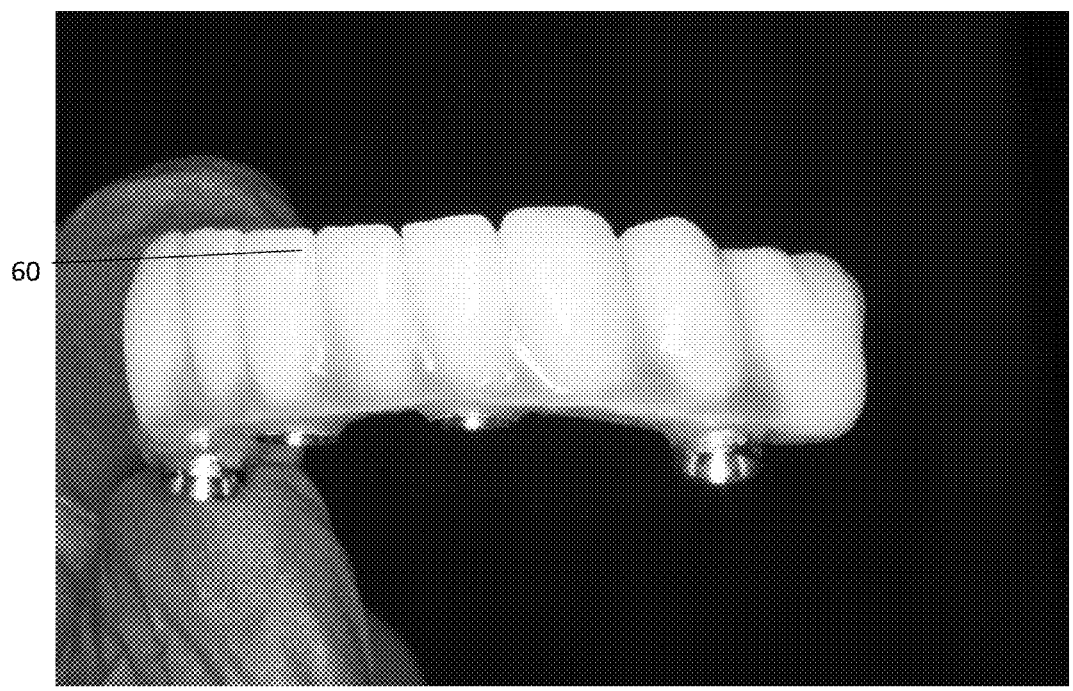
FIG. 37 is a view of the artificial teeth showing the support bars removed and the PMMA artificial teeth polished prior to placement.
Figure 38:
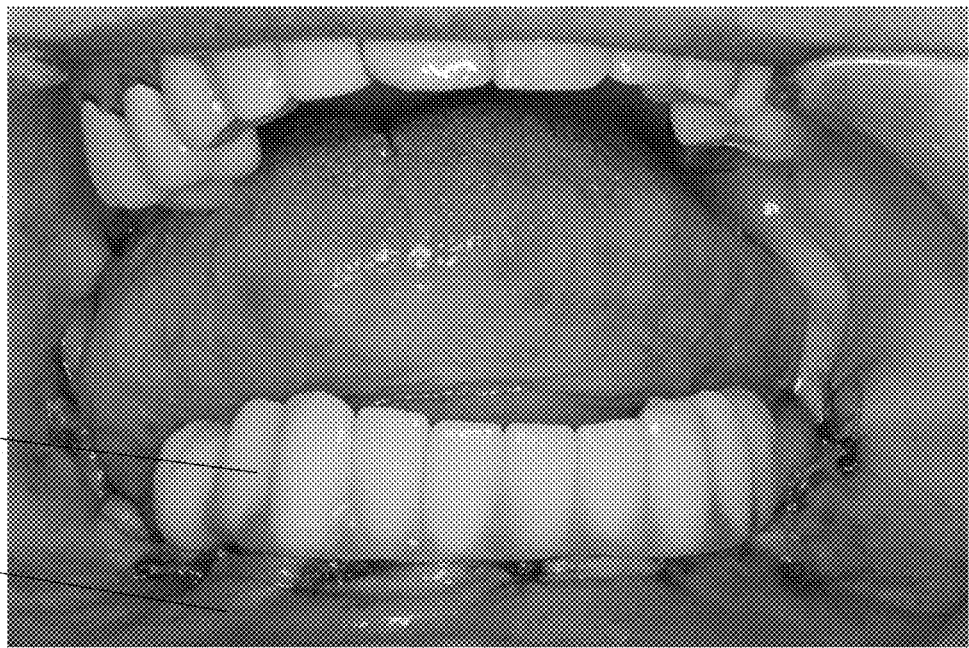
FIG. 38 is a view of the patient's mouth open and the artificial teeth securely fastened to the implanted abutments with the gum tissue stitched in place.
Figure 39:
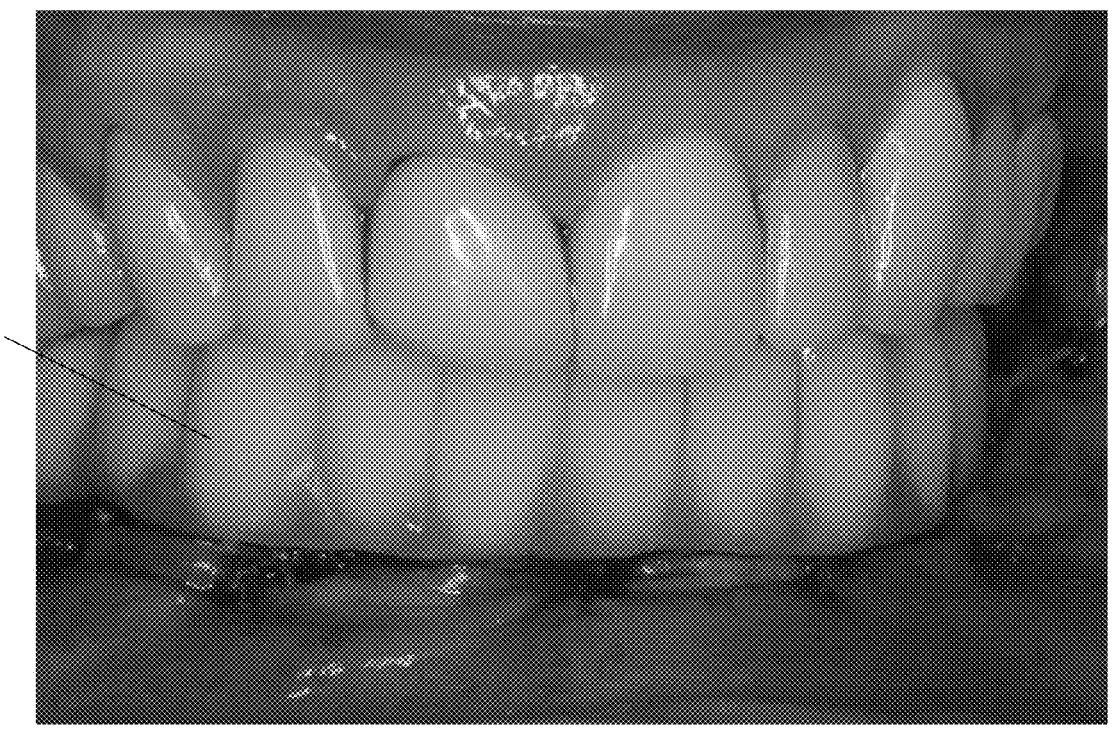
FIG. 39 is a view of the patient's mouth closed partially to show the fit of the artificial teeth after surgery.

The artificial teeth as shown in FIG. 35 have the support bars still positioned on the artificial teeth 60. At this point in time, the surgeon can remove the one or more fasteners 90 and the anatomical guide 20 leaving only the multiunit abutments 94 in the patient's mouth, as shown in FIG. 36. Then the surgeon can suture up the patient's gums 5 and prepare the patient to receive the artificial teeth 60. During this time, technicians can prepare the artificial teeth 60 for implantation by removing the support bars 61, 68 and polishing the teeth so they will have a proper look and have the support bars completely removed as shown in FIG. 37. Once this is accomplished, the artificial teeth 60 are positioned into the patients mouth and screws 91 threadingly engage the multiunit abutments 94 through the cylinder 98 to tighten the artificial teeth 60 firmly against the implanted abutments 94, hidden in FIG. 38, but shown in FIG. 1B. The finished artificial teeth 60 will appear as shown in FIG. 39.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A dental alignment guide system for dental implant placement comprises:

an anatomical guide having an arch shaped structure having a first end and a second end, the arch shaped structure having a curved exterior wall and a curved interior wall extending between the ends, the interior wall formed using a 3D scan of a patient to mimic bone without any gum tissue and configured to abut directly against and be secured to a portion of a labial and/or buccal side of a patient's exposed bone of the alveolar process with soft gum tissue removed or displaced by flapping and the anatomical guide is configured to be received on the patient such that none of the anatomical guide is on the lingual or interior side of the patient's bone, the curved exterior wall having a plurality of fastener openings extending through the arch shaped structure, each fastener opening configured to receive a fastener to secure the anatomical guide to the exposed bone of either the mandible or the maxilla;

a plurality of fasteners, the plurality of fasteners are threaded screws to fasten the anatomical guide to the exposed bone, each threaded screw passing through one of the plurality of fastener openings of the anatomical guide;

a tooth supported guide with a curved structure configured to vertically fit onto a patient's existing teeth having a plurality of connections extending from the curved structure, each of the connections of the plurality of connections being sized to be received and complimentarily fit into one of a plurality of connection apertures on the anatomical guide; and wherein the anatomical guide and the tooth supported guide when connected together form an anatomical guide and tooth supported guide assembly.

2. The dental alignment guide system of claim 1 wherein the anatomical guide and tooth supported guide assembly is configured to be supported vertically by teeth of a patient to align the interior wall of the anatomical guide to abut against the exposed bone prior to securing the anatomical guide with the plurality of fasteners to the exposed bone.

3. The dental alignment guide system of claim 2 wherein the interior wall of the anatomical guide is configured to abut against the exposed bone partially under a ridge between the teeth and the exposed bone at an undercut of the exposed bone and teeth upon securing the anatomical guide to the exposed bone with the plurality of fasteners.

4. The dental alignment guide system of claim 1 wherein the plurality of connections of the tooth supported guide are in a shape of a plurality of support bars, wherein the support bars of the tooth supported guide are in proximity to the first end and the second end of the anatomical guide, each support bar end having an opening at an end and the connection apertures of the anatomical guide has a pair of openings, each opening of the pair of openings being aligned with said support bar end opening and on assembly of the anatomical guide and the tooth supported guide, the aligned openings configured to receive a pin or locking device for coupling the anatomical guide to the tooth supported guide to form the anatomical guide and tooth supported guide assembly.

5. The dental alignment guide system of claim 4 wherein the plurality of support bars of the tooth supported guide are three leg supports including a middle leg support interposed between two leg supports, the middle leg support having the end with a round cross section, the other two leg supports having the ends with either a polygonal cross section having three or more sides or a circular cross-section or any combination thereof.

6. The dental alignment guide system of claim 4 wherein the tooth supported guide further has two support structures spaced from the curved structure, each said support structure spanning between and connecting a pair of adjacent support bars of the plurality of support bars extending from the curved structure.

7. The dental alignment guide system of claim 6 wherein the anatomical guide has a cross-sectional thickness along the arch shaped structure to prevent buckling between the opposing interior wall and exterior wall.

8. The dental alignment guide system of claim 1 wherein the curved structure has a plurality of apertures on the curved structure, the apertures forming windows open to verify tooth position.

9. The dental alignment guide system of claim 1 wherein the tooth supported guide is removably attached to the anatomical guide as the anatomical guide and tooth supported guide assembly.

10. The dental alignment guide system of claim 1 wherein the anatomical guide has a flat outer surface extending between the curved interior wall and the curved exterior wall to provide a bone cutting guide surface to create a reduced bone with teeth removed to receive implants.

11. A dental alignment guide system for dental implant placement comprises:

an anatomical guide having an arch shaped structure having a first end and a second end, the arch shaped structure having a curved exterior wall and a curved interior wall extending between the ends, the interior wall formed using a 3D scan of a patient to mimic bone without any gum tissue and configured to abut directly against and be secured to a portion of a labial and/or buccal side of a patient's exposed bone of the alveolar process with soft gum tissue removed or displaced by flapping and wherein the anatomical guide is configured to be received on the patient such that none of the anatomical guide is on the lingual or interior side of the patient's bone, the curved exterior wall having a plurality of fastener openings extending through the arch shaped structure, each fastener opening configured to receive a fastener to secure the anatomical guide to the exposed bone of either the mandible or the maxilla;

a plurality of fasteners, the plurality of fasteners are threaded screws to fasten the anatomical guide to the exposed bone, each threaded screw passing through one of the plurality of fastener openings of the anatomical guide;

a surgical guide, the surgical guide with a curved structure having a plurality of connections; the curved structure having a plurality of openings extending from an outer surface of the curved structure inwardly to an inner surface of the curved structure, the plurality of openings configured to receive implants or screws for seating the surgical guide, each of the connections of the plurality of connections extending from the curved structure to an end, each end of the connection being sized to be received and complimentarily fit into a plurality of connection apertures on the anatomical guide; and wherein the anatomical guide and the surgical guide when connected together form an anatomical guide and surgical guide assembly.

12. The dental alignment guide system of claim 11 wherein the plurality of connections are a plurality of support bars, wherein the support bars of the surgical guide are in proximity to the first end and the second end of the anatomical guide, each support bar having an opening and the connection apertures of the anatomical guide has a pair of openings, each opening of the pair of opening being aligned with said support bar end opening on assembly of the anatomical guide and the surgical guide to form the anatomical guide and surgical guide assembly, the aligned openings configured to receive a pin or locking device for coupling the anatomical guide to the surgical guide on assembly.

13. The dental alignment guide system of claim 12 wherein the surgical guide is rigidly supported by the connections on the support bars and cantilevered over the anatomical guide forming a space between the surgical guide and the anatomical guide creating a gap, preventing the surgical guide from sitting on a top cutting surface of the anatomical guide while cantilevering over the bone.

14. The dental alignment guide system of claim 11 wherein the surgical guide has the outer surface with the plurality of openings, each opening having a guide tube, each guide tube being received and positioned in one of the plurality of openings to direct a placement of a drill and an implant into a reduced bone.

15. The dental alignment guide system of claim 14 further comprises:
prosthetic artificial teeth,
the prosthetic artificial teeth being configured for attachment to the anatomical guide after the surgical guide is removed.

16. The dental alignment guide system of claim 15 further comprises:
a plurality of implants, the implants configured to pass through the guide tubes of the surgical guide.

17. The dental alignment guide system of claim 16 further comprises:
an implant driver; and
a drill, the drill being guided by the guide tubes to drill into a reduced bone prior to the implants being driven into the reduced bone with the implant driver, the implants being guided by the guide tube and fixed to the bone at a desired angle, depth and rotation, rotation being controlled by aligning markers on the implant driver to markers on the surgical guide at a depth stop.

18. The dental alignment guide system of claim 17 further comprises:
a prosthetic seat made with openings aligned with the implants in the reduced bone when the surgical guide is removed, the prosthetic seat being configured to be positioned on the reduced bone with identifying markers for abutment pieces to be attached to the implants in the reduced bone between the reduced bone and prosthetic artificial teeth; and
abutments for attachment to the implants, wherein each abutment has one or more alignment flats or slots and the prosthetic seat is marked to indicate an alignment location for the flats or slots to control rotation to a desired angle.

19. The dental alignment guide system of claim 18 wherein each abutment has internal threads.

20. The dental alignment guide system of claim 19 further having a plurality of cylinders held by the abutments wherein each abutment has an exposed end configured to receive and temporarily hold one of the plurality of cylinders, each cylinder being pre-cut to a desired length, the cylinders are transferred from the abutments by adhesively curing into a plurality of holes in the prosthetic artificial teeth, once cured the cylinders are permanently attached to the prosthetic artificial teeth and removed from the abutments.

21. The dental alignment guide system of claim 20 wherein upon removal of the surgical guide from the anatomical guide after bone reduction, the dental alignment guide system further comprises the prosthetic artificial teeth, the prosthetic artificial teeth has a plurality of connections, each connection configured to align with the connection aperture of the anatomical guide to form an anatomical guide and prosthetic artificial teeth assembly.

22. The dental alignment guide system of claim 21 further comprises: a plurality of straws, a straw being inserted into an opening in an open end of the cylinder to occlude the opening.

23. The dental alignment guide system of claim 21 further comprises: a plurality of screws configured to pass through the cylinders and thread into the abutments thereby securing the artificial teeth to reduced bone.

24. The dental alignment guide system of claim 11 further comprises:
an analog model, the analog model being a structure replicating a patient's reduced bone with holes representing where implant placements will be for abutment placement and titanium cylinder placement and prosthetic teeth, the analog model has a pair of attachment openings configured to receive an articulation piece allowing the surgeon to ensure proper fit prior to implant placement into a reduced and prepared bone;
an articulation piece, the articulation piece has a pair of attachment posts for attachment into the pair of attachment openings on the analog model to form an analog model and articulation piece assembly; and
wherein the articulation piece replicates the patient's teeth and bone that existed prior to a bone reduction to provide for alignment and articulation and is configured to ensure that bone is properly prepared so alignment of the jaw is such that the removed existing teeth can be replicated, the combination of the analog model and articulation piece mimics what will happen in a patient, the articulation piece ensures for a surgeon that the bone after being reduced using the anatomical guide and surgical guide assembly is properly prepared.

25. The dental alignment guide system of claim 24 further comprises:
a tooth supported guide with a curved structure configured to vertically fit onto a patient's existing teeth having a plurality of connections extending from the curved structure, each of the connections of the plurality of connections being sized to be received and complimentarily fit into one of the plurality of connection apertures on the anatomical guide; and
an anatomical model, the anatomical model being a structure duplicating a patient's teeth and exposed alveolar process with soft tissue removed to replicate the patient's teeth and mandible or maxilla prior to any teeth extraction or bone reduction, the anatomical model configured to provide the surgeon a way to insure proper alignment by placing the tooth supported guide and the anatomical guide assembly onto the anatomical model.

26. The dental alignment guide system of claim 25 wherein the anatomical model is a three-dimensional model made by combining laser scanning of the patient's teeth with a CT image of the patient's anatomy and 3D printing.

* * * * *